United States Patent
Matakawa et al.

(10) Patent No.: US 10,105,364 B2
(45) Date of Patent: Oct. 23, 2018

(54) INK COMPOSITION, PRINTED MATTER AND PRINTING METHOD

(71) Applicant: T&K Toka Co., Ltd., Saitama (JP)

(72) Inventors: Shuichi Matakawa, Saitama (JP); Shuichi Watanabe, Saitama (JP)

(73) Assignee: T&K TOKA CO., LTD., Saitama (JP)

( * ) Notice: Subject to any disclaimer, the term of this patent is extended or adjusted under 35 U.S.C. 154(b) by 0 days.

(21) Appl. No.: 15/120,175

(22) PCT Filed: Feb. 20, 2015

(86) PCT No.: PCT/JP2015/054761
§ 371 (c)(1),
(2) Date: Aug. 19, 2016

(87) PCT Pub. No.: WO2015/129572
PCT Pub. Date: Sep. 3, 2015

(65) Prior Publication Data
US 2017/0368064 A1     Dec. 28, 2017

(30) Foreign Application Priority Data

Feb. 25, 2014   (JP) ................. 2014-034106
Oct. 6, 2014    (JP) ................. 2014-205446

(51) Int. Cl.
*G01D 11/00*   (2006.01)
*A61K 31/506*  (2006.01)
(Continued)

(52) U.S. Cl.
CPC ........ *A61K 31/506* (2013.01); *A61K 31/5355* (2013.01); *A61K 45/06* (2013.01);
(Continued)

(58) Field of Classification Search
None
See application file for complete search history.

(56) References Cited

U.S. PATENT DOCUMENTS

| | | | |
|---|---|---|---|
| 2003/0157338 A1* | 8/2003 | Kondo | B32B 27/40 428/423.3 |
| 2008/0199804 A1* | 8/2008 | Oohashi | B41C 1/1008 430/270.1 |

FOREIGN PATENT DOCUMENTS

| | | |
|---|---|---|
| GB | 1563669 A | 3/1980 |
| JP | 53098385 A | 8/1978 |

(Continued)

OTHER PUBLICATIONS

Supplementary European Search Report; dated Sep. 29, 2017 for EP Application No. EP15755405.
(Continued)

*Primary Examiner* — Erica Lin
(74) *Attorney, Agent, or Firm* — Mendelsohn Dunleavy, P.C.

(57) ABSTRACT

Provided is an ink composition less likely to cause offset and sticking. Provided is a printed matter and a printing method using such ink composition. The ink composition includes a (meth) acrylic resin and a drying oil, the (meth)acrylic resin: containing at least 40% by weight or more of a structural unit derived from (meth)acryl monomer having a straight-chain alkyl group having 4 or more carbon atoms, branched alkyl group having 4 or more carbon atoms, or cyclic alkyl group having 4 or more carbon atoms (1); having a glass transition temperature of 63° C. to 180° C. (2); and having a weight-average molecular weight of 1000 to 80,000 (3).

14 Claims, 3 Drawing Sheets

(51) Int. Cl.

| | | |
|---|---|---|
| *C09D 11/06* | (2006.01) | |
| *C09D 11/107* | (2014.01) | |
| *C09D 11/12* | (2006.01) | |
| *A61K 31/5355* | (2006.01) | |
| *A61K 45/06* | (2006.01) | |
| *C07D 403/04* | (2006.01) | |
| *C07D 413/14* | (2006.01) | |

(52) U.S. Cl.
CPC ......... *C07D 403/04* (2013.01); *C07D 413/14* (2013.01); *C09D 11/06* (2013.01); *C09D 11/107* (2013.01); *C09D 11/12* (2013.01)

(56) References Cited

FOREIGN PATENT DOCUMENTS

| JP | 62005468 A | 1/1987 |
|---|---|---|
| JP | S62143984 A | 6/1987 |
| JP | 06116525 A | 4/1994 |
| JP | H08259868 A | 10/1996 |
| JP | H11228899 A | 8/1999 |
| JP | 2002155227 A | 5/2002 |
| JP | 2002226754 A | 8/2002 |
| JP | 2003147253 A | 5/2003 |
| JP | 2005264107 A | 9/2005 |
| JP | 2006206667 A | 8/2006 |
| JP | 2010006993 A | 1/2010 |
| JP | 2010047670 A | 3/2010 |

OTHER PUBLICATIONS

Andrews, R. J., et al., "Glass transition temperatures of polymers;" Wiley Database of Polymer Properties; 2003; pp. VI/193-VI/217.

International Search Report and Written Opinion; dated May 26, 2015 for PCT Application No. PCT/JP2015/054761.

International Preliminary Report on Patentability; dated Sep. 9, 2016 for PCT Application No. PCT/JP2015/054761.

KR Office Action; dated May 8, 2018 for KR Application No. 10-2016-7022844.

JP Notification of Reasons for Refusal; dated Jul. 10, 2018 for JP Application No. 2016-505177.

IN First Examination Report; dated Aug. 29, 2018 for IN Application No. 201647032151.

* cited by examiner

INK COMPOSITION, PRINTED MATTER AND PRINTING METHOD

TECHNICAL FIELD

This invention relates to an ink composition, a printed matter and a printing method, preferably to an ink composition used for offset printing, and further to a printed matter and a printing method using such ink composition.

BACKGROUND ART

Ink composition for offset printing is typically composed of a colorant represented by pigment; a binder resin represented by rosin-modified phenol resin and rosin-modified maleic resin; a drying oil such as tung oil, linseed oil and soybean oil, used for forming a coated film; a dryer used as a catalyst for promoting oxidative polymerization (dry curing using aerial in the air); and a petroleum solvent such as mineral oil. The ink composition may be optionally added with a variety of additives, aiming at improving suitability to printing related to printing presses.

An exemplary method of printing using an ink composition for offset printing of books, posters, calendars and so forth will now be explained. FIG. 1 is a schematic drawing for explaining an exemplary method of printing using the ink composition for offset printing, where reference numeral 1 stands for a petroleum solvent, 2 for a printing pacer, 3 for oxygen, 4 for a colorant, 5 for a binder resin, and 6 for a drying oil. Now as illustrated in FIG. 1, printing follows processes of allowing the petroleum solvent 1 contained in the ink composition for offset printing to permeate into the printing paper 2, allowing the residual components which remain on the surface of the printing paper to be oxidized by aerial in the air 3, polymerized and dried, to thereby form a solid coating on the surface of the printing paper. In FIG. 1, (1) illustrates a state immediately after printing, (2) illustrates a state in the middle way of set drying (which means permeation of solvent into paper, also referred to as permeation drying), and (3) illustrates a state after completion of oxidative polymerization and drying. Immediately after the printing (1), an ink composition layer applied to the surface of the printed matter does not dry. In the step of set drying (2), the solvent in the ink composition permeates into the printing paper, and thereby the ink composition increases the viscosity. Although the ink composition layer becomes somewhat durable against pressurizing owing to the thus increased viscosity, the set drying (2) is not yet a step of complete drying. Although the set drying (2) and the oxidative polymerization and drying (3) can proceed concurrently, the set drying completes within a time scale of several minutes, meanwhile the oxidative polymerization and drying needs several hours. It takes only several seconds for the printing paper to be input and output to and from a printing press. The printing matter is, therefore, output from, the printing press before being fully processed by the steps of set drying (2) and oxidative polymerization and drying (3). As a consequence, the printed matters when stacked (or column-stacked) after the printing may adhere to each other. In particular, adhesion of the ink, before being thoroughly set-dried, onto the back face of the printed matter is called "offset". Adhesion of the ink onto the back face of the column-stacked printed matters, due to delayed drying of the ink and pressurizing on the paper, is called "sticking". Meanwhile, adhesion of the printed faces of the column-stacked printed matters so as to form a block, due to re-softening of the ink even having once been completely dried, is called "blocking".

In these years, an ink composition having a reduced content of, or even no, petroleum solvent has been attracting public attention, from the environmental, or safety and hygienic points of view, and is becoming more popularly used. As one example of such ink composition, efforts have been made to replace a part of, or all of, petroleum solvent with a drying oil such as soybean oil. The ink composition, however, often tends to delay elimination of the petroleum solvent contained therein, as the content of drying oil such as soybean oil increases, and to delay permeation into the printing paper. This unfortunately worsens offset or sticking, characterized by adhesion of ink onto the back face of printing paper.

A popular way to avoid offset and blocking is to scatter a powder, such as corn starch, over the printing paper immediately after printing. Such scattering of powder, however, degrades the work environment due to dusting of the powder per se, shortens the cleaning cycles, and lowers the production efficiency. It also causes so-called "scaling", which is an accidental fall of the powder, having been accumulated on a delivery portion inside the printing press, onto the printed matter during printing. The powder not only degrades the quality of printed product, but also inhibits PP lamination in the post process, which is a step of laminating a polypropylene sheet onto the printed matter. It has also been pointed out that the fine powder entrained, inside the printing press may heavily wear the mechanical parts, may induce failure, and may shorten the service life of the press.

As solutions to solve this problem, there have been proposed methods of incorporating a predetermined amount of a polymer having a solubility parameter of 19 $(MPa)^{1/2}$ or smaller, and compatible with the solvent component, into the ink composition for offset printing (Patent Literature 1, Patent Literature 2); a method of incorporating a solvent composed of a plant oil component and liquid paraffin into the ink composition for offset printing (Patent Literature 3); and a method of incorporating a composition for planographic liquid which contains an acrylic copolymer having a glass transition temperature of 20° C. or higher and having a weight-average molecular weight of 30,000 to 500,000, and an aliphatic hydrocarbon (Patent Literature 4).

Also from the environmental point of view, there has been a diversified trend of printing paper, including non-wood pulp paper made of fiber of kenaf or rice straw, and decorative paper called fancy paper, rather than recycled paper recycled from used paper or wood pulp. This sort of printing paper, however, allows therein only a slow permeation of the solvent contained in the ink composition, making the paper less dryable, and more likely to cause problems such as offset and sticking.

A UV curable ink composition has been proposed to solve the problem (Patent Literature 5). The UV curable ink composition can dry and cure under UV irradiation within a very short time, and will have high friction resistance, anti-blocking performance, and anti-offset performance, without needing the powder spray.

The UV curable ink composition, however, needs an additional UV irradiation equipment, and is not economical. The composition also needs a special UV curable monomer, oligomer and photo-polymerization initiator, making the ink composition expensive. The ink composition is not preferable also from the viewpoint of energy consumption, since it requires not only electric power for operating the printing press, but also electric power fed to a UV lamp used for irradiating UV light.

Also there is proposed a method of using an OP varnish typically containing coarse processed starch or resin (Patent Literature 6). The method is, however, disadvantageous not only because the OP varnish is clear and the offset is not recognizable if occurred, on the printing paper, and also because the offset may occur on the printing paper on which the ink can set-dry only slowly, in the process of stacking the printed matters during printing.

Patent Literature 7 describes mixing of an anti-blocking powder into a printing ink.

Patent Literature 8 discloses an ink composition for dry planographic printing, which contains a homopolymer of a (meth) acrylate ester produced from acrylic acid or methacrylic acid, reacted with a monohydric alcohol having a number-average molecular weight of 5 to 40. A polymer of 2-ethylhexyl acrylate described in Patent Literature 8 has a glass transition temperature of 0° C. or below.

Patent Literature 9 describes a printing ink which contains a copolymer composed of isobornyl methacrylate and ethylenic unsaturated monomer, having a weight-average molecular weight of 4,000 to 12,000, and a glass transition temperature of 50 to 120° C.

Patent Literature 10 discloses a resin composition for ink, which contains an acrylic copolymer containing 4-t-butylcyclohexyl (meth) acrylate monomer and a vinyl-based monomer having a functional group. Patent Literatures 9 and 10 employ a printing system capable of forming an ink composition film without using a drying oil.

In the printing market today, requests for shorter delivery are increasing acceleration. In such circumstances, there are strong needs for improving the productivity without any new facility investment, improving the environmental hygiene which may be degraded by the scattered powder around the printing press, and elongating the mechanical service life of the printing press and the peripheral equipment.

CITATION LIST

Patent Literature

[Patent Literature 1] JP-A-2002-155227
[Patent Literature 2] JP-A-2003-147253
[Patent Literature 3] JP-A-2002-226754
[Patent Literature 4] JP-A-2010-6993
[Patent Literature 5] JP-A-H11-228899
[Patent Literature 6] JP-A-2010-47670
[Patent Literature 7] JP-A-2006-206667
[Patent Literature 8] JP-B-S62-5468
[Patent Literature 9] JP-A-S53-98385
[Patent Literature 10] JP-A-2005-264107

SUMMARY OF THE INVENTION

Technical Problem

This invention is aimed at solving the problems above, and an object of the invention is to provide an ink composition less likely to cause offset and sticking. Another object of this invention is to provide a printed matter and a printing method using such ink composition.

Solution to Problem

Considering the above-described problems, the present inventors found from our investigations that the problems may be solved by the means <1> or <6> below, and preferably by the means <2> to <5> and <7> to <15>.

<1> An ink composition comprising a (meth)acrylic resin and a drying oil, the (meth)acrylic resin: containing at least 40% by weight or more of a structural unit derived from (meth)acryl monomer having a straight-chain alkyl group having 4 or more carbon atoms, branched alkyl group having 4 or more carbon atoms, or cyclic alkyl group having 4 or more carbon atoms (1); having a glass transition temperature of 63° C. to 180° C. (2); and having a weight-average molecular weight of 1000 to 80,000 (3).

<2> The ink composition of <1>, which contains the (meth) acrylic resin in a content of 1 to 10% by weight.

<3> The ink composition of <1>, which contains the (meth) acrylic resin in a content of 2 to 6% by weight.

<4> The ink composition of <1>, which contains 1 to 10% by weight of the (meth)acrylic resin, 20 to 35% by weight of a binder resin, 10 to 40% by weight of the drying oil, 15 to 40% by weight of a solvent, 0.01 to 3% by weight of a dryer, and, 0.1 to 5% by weight of a wax.

<5> The ink composition of <1>, which contains 2 to 6% by weight of the (meth)acrylic resin, 25 to 30% by weight of a binder resin, 15 to 35% by weight of the drying oil, 20 to 30% by weight of a solvent, 0.5 to 1.5% by weight of a dryer, and, 0.5 to 4% by weight of a wax.

<6> An ink composition containing a particle having an average size of 3.0 to 17.5 µm, and; relative to the ink composition, containing 0.01 to 1% by weight of a spherical particle having a particle size of 1.0 to 20.2 µm, and 0.1% by weight or less of a particle having a particle size exceeding 20.2 µm.

<7> The ink composition of <6>, further containing 20 to 45% by weight of a binder resin, 10 to 45% by weight of a drying oil, 15 to 45% by weight of a solvent, 0.01 to 3% by weight of a dryer, and, 0.1 to 5% by weight of a wax.

<8> The ink composition of any one of <1> to <5>, further containing a particle having an average size of 3.0 to 17.5 µm, and; relative to the ink composition, containing 0.01 to 1% by weight of a spherical particle having a particle size of 1.0 to 20.2 µm, and 0.1% by weight or less of a particle having a particle size exceeding 20.2 µm, <9> The ink composition of any one of <1> to <5>, containing 1 to 10% by weight of the (meth)acrylic resin, 20 to 35% by weight of a binder resin, 10 to 40% by weight of a drying oil, 15 to 40% by weight of a solvent, 0.01 to 3% by weight of a dryer, 0.1 to 5% by weight of a wax, and 0.01 to 1% by weight of a spherical particle having a particle size of 1.0 to 20.2 µm, wherein the composition contains a particle having a particle size exceeding 20.2 µm in a content of 0.1% by weight or less.

<10> The ink composition of any one of <1> to <9>, further containing 5 to 35% by weight of a colorant, <11> The ink composition of any one of <6> to >10>, wherein the spherical particle is at least one species selected from an olefinic particle, a styrene-based particle, a phenolic particle, a silicone-based particle, a urethane-based particle and an acrylic particle.

<12> The ink composition of any one of <1> to <11>, which is used for offset printing.

<13> An ink composition used for a printing method by which a solvent contained in the ink composition described in any one of <1> to <5> and <7> to <9> is allowed to permeate into a printing paper, and residual components which remain on a surface of the printing pacer are allowed to be oxidized by aerial in the air, polymerized and dried, so as to form a solid coating on the surface of the printing paper.

<14> A printed matter obtained by using the ink composition described in any one of <1> to <13>.
<15> A printing method using the ink composition described in any one of <1> to <13>.

Advantageous Effects of Invention

According to this invention, it now became possible to provide an ink composition less likely to cause offset and sticking. It also became possible to provide a printed matter and a printing method using such ink composition.

DESCRIPTION OF EMBODIMENTS

Figure 1:
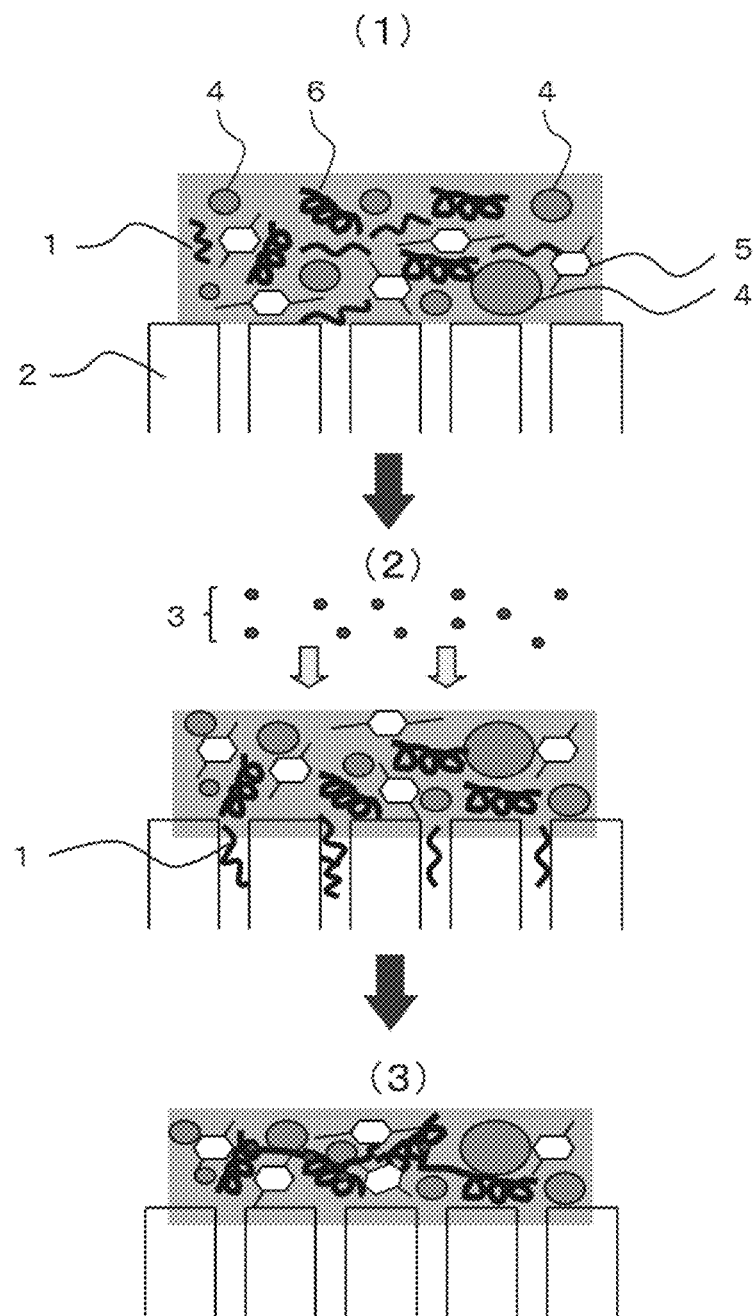
FIG. 1 A schematic drawing illustrating a printing mechanism using an ink composition in offset printing.

This invention will be detailed below.

Note that, in this specification, all numerical ranges given in the form of "to", preceded and succeeded by numerals, shall be defined to contain these numerals as the lower and upper limit values. In this specification, all "groups", such as alkyl group, may have a substituent, or need not to have a substituent, unless otherwise specifically noted. When the group is specified by the number of carbon atoms, such number of carbon atoms shall include the number of carbon atoms contained in the substituent.

In this specification, (meth)acrylate collectively means acrylate and methacrylate. For example, methyl (meth) acrylate collectively means methyl acrylate and methyl methacrylate.

The first ink composition of this invention contains a (meth)acrylic resin and a drying oil, where the (meth)acrylic resin: (1) contains at least 40% by weight or more of a structural unit derived from (meth) acryl monomer having a straight-chain, branched or cyclic alkyl group having 4 or more carbon atoms; (2) having a glass transition temperature of 63° C. to 180° C.; and (3) having a weight-average molecular weight of 1000 to 80,000. By using the first-ink composition, it now becomes possible to suppress offset and blocking, also to shorten the set-drying time, and to effectively suppress the viscosity of ink composition from varying.

A second ink composition of this invention contains 0.01 to 1% by weight of a spherical particle having a particle size of 1.0 to 20.2 μm, and 0.1% by weight or less of a particle having a particle size exceeding 20.2 μm. With the second ink composition, it now becomes possible to provide the ink composition having a small slip angle, or, being highly slippery and less likely to cause offset.

In particular, with the ink composition which satisfies both requirements of the first ink composition and the second ink composition, the waiting time for drying may be reduced, so that the waiting time after paper cutting and printing on one surface, and before the next printing on the other surface may be reduced, leading to a great improvement in productivity.

The ink composition of this invention is preferably used as an ink composition for offset printing. The ink composition of this invention can dispense with powder having often been sprayed to avoid offset in offset printing, or can dramatically reduce the amount of consumption thereof. This not only improves the work environment, but is also effective enough to prevent the printing press and the peripheral equipment from degrading.

Offset printing in this invention is also referred to as planographic printing. The printing method includes two types of printing, one of which is wet offset printing theoretically based on repulsion between a lipophilic ink composition and a hydrophilic damping water; and waterless offset printing in no need of damping water, as a result of treatment of the surface of the printing plate to impart water repellency. These methods of offset printing are characterized in that the ink composition contained in an ink pot is transferred from a form roller via a plurality of rollers to the printing plate, then transferred from the printing plate to a rubber blanket, then from the rubber blanket to a printing paper or so. The ink composition of this invention is applicable both to an ink composition for wet offset printing, and an ink composition for waterless offset printing.

<(Meth)Acrylic Resin>

Paragraphs below will describe the (meth)acrylic resin contained in the ink composition of this invention, which (1) contains at least 40% by weight or more of a structural unit derived from (meth) acryl monomer having a straight-chain, branched or cyclic alkyl group having 4 or more carbon atoms; (2) has a glass transition temperature of 63° C. to 180° C.; and (3) has a weight-average molecular weight of 1000 to 80,000.

The (meth) acrylic resin may be a homopolymer of (meth) acrylate; or may be a copolymer of (meth)acrylate and other monomer having a vinyl group, that is, a polymer obtained by polymerization with a compound which allows polymerization to proceed as a result of cleavage of its carbon-carbon double bond.

The (meth)acryl monomer usable for the manufacture of the (meth) acrylic resin is not specifically limited so long as it satisfies the aforementioned requirements (1) to (3).

Requirement (1) is defined to make the (meth)acrylic resin soluble to any of particularly preferred, solvents described, later, which are aliphatic and/or alicyclic hydrocarbon solvents.

The number of carbon atoms of the straight-chain, branched or cyclic alkyl group having 4 or more carbon atoms is preferably 4 to 30, more preferably 4 to 20, and even more preferably 4 to 15. The straight-chain, branched or cyclic alkyl group having 4 or more carbon atoms is preferably a branched or cyclic alkyl group, and more preferably a cyclic alkyl group.

The amount of the structural unit derived from (meth) acryl monomer, mentioned above to be at least 40% by weight or more, is used within the range that the finally obtained (meth)acrylic resin will have a glass transition temperature of 63° C. to 180° C. The amount of the structural unit derived from (meth)acryl monomer is preferably 60% by weight or more, and more preferably 70% by weight or more. Although the upper limit value may be 100% by weight, it is preferably 99.5% by weight or less.

The (meth)acrylic resin used in this invention has a glass transition temperature of 63° C. to 180° C. The lower limit of the glass transition temperature is preferably 70° C. or higher, more preferably 80° C. or higher, even more preferably 90° C. or higher, and yet more preferably 100° C. or higher. The upper limit value of the glass transition temperature is preferably 170° C. or lower, and more preferably 160° C. or lower. The glass transition temperature of the (meth)acrylic resin may be determined using equation (1) below, according to the description in T. G. Fox, *Bull. Am. Phys. Soc.*, 1, (3), 123 (1956).

Equation (1)

$$1/Tg = w1/Tg1 + w2/Tg2$$ [Mathematical Formula 1]

Each of Tg1, Tg2, . . . represents the glass transition temperature (K) of a homopolymer composed of each monomer unit which composes the (meth) acrylic resin, and each of w1, w2 . . . represents the weight-fraction of each monomer unit which composes the (meth) acrylic resin.

The (meth)acrylic resin used in this invention has a weight-average molecular weight of 1,000 to 80,000. The lower limit value of the weight-average molecular weight is preferably 2,000 or larger, and more preferably 3,000 or larger. The upper limit value of the weight-average molecular weight is preferably smaller than 60,000, more preferably 40,000 or smaller, even more preferably 31,000 or smaller, yet more preferably smaller than 30,000, yet more preferably 20,000 or smaller, and particularly 19,500 or smaller.

If the weight-average molecular weight is smaller than 1,000, the set-dryability in offset printing may degrade. Meanwhile, if it exceeds 80,000, the resultant (meth)acrylic resin may become highly viscous, may become difficult to handle, and may need an increased amount of solvent if it has been degraded in compatibility or in need of dilution, enough to damage the practicality.

The weight-average molecular weight in this invention is determined by measurement using Shodex System 21H from Showa Denko K.K., having two Shodex KF-85L columns from Showa Denko K.K. connected in series, using tetrahydrofuran as an eluent, and using standard polystyrene from Japan Analytical Industry Co., Ltd. as standard substances for preparing a calibration curve.

The (meth)acrylic resin used in this invention is preferably such that a homopolymer of the (meth)acryl monomer, as the major constitutive unit thereof, will have a glass transition temperature (Tg) of 63° C. to 180° C. The (meth) acryl monomer preferably used in this invention is exemplified by 4-tert-butyl methacrylate (Tg: 107° C., measured for homopolymer, same will apply hereinafter), tert-butylcyclohexyl methacrylate (Tg: 125° C.), cyclohexyl methacrylate (Tg: 83° C.), isobornyl methacrylate (Tg: 155° C.), adamantyl methacrylate (Tg: 170° C.), dicyclopentenyl methacrylate (Tg: 170° C.), dicyclopentanyl methacrylate (Tg: 175° C.), isobornyl acrylate (Tg: 94° C.), dicyclopentenyl acrylate (Tg: 120° C.), dicyclopentanyl acrylate (Tg: 120° C.), and adamantyl acrylate (Tg: 115° C.). Among them, tert-butyl methacrylate, cyclohexyl methacrylate, isobornyl methacrylate, and isobornyl acrylate are particularly preferable from the viewpoint of availability.

Only a single species of the (meth) acryl monomer may be used, or two or more species may be used in combination.

The (meth) acrylic resin used in this invention may contain other monomer unit besides the (meth)acryl monomer, without departing from the scope of this invention. Such other monomer is exemplified as follows, wherein only a single species may be used, or two or more species may be used in combination. The content of the other monomer unit, when contained, is preferably 20 to 40% by weight of the total monomer units.

Styrene-based monomer such as styrene, p-methylstyrene, p-chloromethylstyrene, and vinyl toluene;

(meth)acryl monomers each having a hydrocarbon group, such as methyl (meth)acrylate, ethyl (meth)acrylate, n-propyl (meth)acrylate, and i-propyl (meth)acrylate, which do not satisfy the aforementioned requirement of "(1) (meth) acryl monomer having a straight-chain, branched or cyclic alkyl group having 4 or more carbon atoms";

(meth)acryl monomers each having a halogenated hydrocarbon group, obtained by substituting the hydrocarbon group possessed by the (meth) acryl monomer with a halogen atom such as fluorine, chlorine, etc.;

silicon-containing (meth)acryl monomers such as tris (trimethylsiloxy)silylpropyl (meth)acrylate, (meth)acryloxypropyl poly(n=2 to 400)-dimethylsiloxane, etc.;

vinyl ester-based monomer each having an optionally substituted hydrocarbon group, such as vinyl acetate, vinyl propionate, vinyl butyrate, vinyl caproate, vinyl caprylate, vinyl laurate, vinyl myristate, vinyl stearate, vinyl cyclohexanecarboxyrate, vinyl pivalate, vinyl 2-ethylhexanoate, vinyl monochloroacetate, vinyl benzoate, and vinyl ester of branched monocarboxylic acid (VeoVa, from Momentive Performance Materials, Inc.);

acrylonitrile-based monomers such as acrylonitrile and methacrylonitrile;

vinyl ether-based monomers each having a hydrocarbon group, such as ethyl vinyl ether, n-propyl vinyl ether, i-propyl vinyl ether, n-butyl vinyl ether, i-butyl vinyl ether, 2-ethylhexyl vinyl ether, and cyclohexyl vinyl ether;

(meth)acrylamide-based monomers such as (meth)acrylamide, N-methyl (meth)acrylamide, N,N-dimethyl (meth) acrylamide, N-ethyl (meth)acrylamide, N,N-diethyl (meth) acrylamide, and N-isopropyl (meth)acrylamide;

acidic vinyl compound-based monomers such as (meth) acrylic acid, crotonic acid, maleic acid, fumaric acid, itaconic acid, citraconic acid, 4-vinylbenzoic acid, p-vinylbenzenesulfonic acid, 2-(meth)acryloyloxyethanesulfonic acid, and mono{2-(meth)acryloyloxyethyl}acid phosphate;

hydroxyl group-containing monomers such as p-hydroxymethylstyrene, 2-hydroxyethyl (meth)acrylate, 2-hydroxypropyl (meth)acrylate, 3-hydroxypropyl (meth)acrylate, 2-hydroxybutyl (meth) acrylate, 4-hydroxybutyl (meth) acrylate, di-2-hydroxyethyl fumarate, polyethylene glycol (meth)acrylate or polypropylene glycol (meth)acrylate, or t-caprolactone adduct of these compounds; adduct of ε-caprolactone with α,β-etylenic unsaturated carboxylic acid such as (meth)acrylic acid, crotonic acid, maleic acid, fumaric acid, itaconic acid, and citraconic acid; hydroxyalkyl esters of these α,β-ethylenic unsaturated carboxylic acid; and adducts of these α,β-ethylenic unsaturated carboxylic acid with epoxy compounds such as butylglycidyl ether, phenyl glycidyl ether, allyl glycidyl ether, 2-ethylhexylglycidyl ether, lauryl glycidyl ether, tridecyl glycidyl ether, tetradecyl glycidyl ether, pentadecyl glycidyl ether, and glycidyl ester of branched monocarboxylic acid (Cardura, from Momentive Performance Materials, Inc.);

epoxy group-containing monomers such as glycidyl (meth)acrylate, 3,4-epoxycyclohexyl methyl (meth)acrylate, and 3,4-epoxyvinylcyclohexane;

alkoxysilyl group-containing monomer such as vinyl trimethoxysilane, γ-(meth)acryloxypropyl trimethoxysilane, γ-(meth)acryloxypropyl triethoxysilane, and γ-(meth)acryloxypropylmethyl dimethoxysilane; and other monomers, including olefinic monomers such as ethylene and propylene; halogenated olefinic monomer such as vinyl chloride, vinylidene chloride, vinyl bromide, vinyl fluoride, vinylidene fluoride, tetrafluoroethylene, and chlorotrifluoroethylene; maleimide, and vinylsulfone.

Among other monomers, from the viewpoint of easiness of copolymerization during the manufacture, it is particularly preferable to use styrene-based monomer and/or the aforementioned (meth)acryl monomer which does not satisfy the requirement of "(1) (meth)acryl monomer having a straight-chain, branched or cyclic alkyl group having 4 or more carbon atoms".

Method of manufacturing the (meth)acrylic resin of this invention may be any of known methods widely practiced. For the specific case where the final application thereof is an ink composition for offset printing, radical solution polymerization is the most convenient and particularly preferable.

Solvent used when the (meth)acrylic resin is manufactured based on the radical solution polymerization is exemplified by, but not specifically limited to, aromatic hydrocarbons such as toluene, xylene, and aromatic hydrocarbon compounds (Solvesso 100, Solvesso 150, Solvesso 200; from Exxon Mobil Corporation); aliphatic or alicyclic hydrocarbons such as n-hexane, n-heptane, cyclohexane, methylcyclohexane, octane, mineral spirit, and kerosene; ester-based compounds such as ethyl acetate, n-butyl acetate, i-butyl acetate, and butyl cellosolve acetate; methyl ester, n-butyl ester, i-butyl ester, n-octyl ester, 2-ethylhexyl ester, mono to triesters of trimethylolpropane, mono to tetraesters of pentaerythritol, and mono to hexaesters of dipentaerythritol of fatty acids obtained from plant oils exemplified by soybean oil, recycled soybean oil, rapeseed oil, coconut oil, hemp seed, oil, linseed oil, olive oil, kaya (Japanese torreya nuts) oil, tung oil, poppy seed oil, sesame oil, safflower oil, rice bran oil, palm oil, castor oil, dehydrated castor oil, sunflower oil, cottonseed oil, and tall oil, or from animal oils exemplified, by beef tallow and lard; alcohol-based compounds such as methanol, ethanol, n-propanol, i-butanol, ethylene glycol, propylene glycol, ethyl cellosolve, butyl cellosolve; and ketone-based compounds such as acetone, methyl ethyl ketone, methyl isobutyl ketone, methyl isoamyl ketone, cyclohexanone, and isophorone. The solvent is preferably exemplified by aromatic hydrocarbon compound, aliphatic and alicyclic hydrocarbon compound. Aliphatic or alicyclic hydrocarbon compound, is particularly preferable if the ink composition for offset printing is intended as a final application. More specifically, also petroleum solvents described later may be used.

The (meth)acrylic resin used in this invention may be manufactured by any of well-known methods using a variety of known radical polymerization initiator such as azo-based compound and peroxide-based compound. Polymerization time is selected within, but not specifically limited to, the range from 1 to 48 hours or around, from the industrial viewpoint. Also polymerization temperature is typically, but not specifically limited to, 30 to 200° C., and preferably 60 to 150° C.

The lower limit, value of the content of the (meth) acrylic resin in this invention is preferably 1% by weight or above, more preferably 2% by weight or above, and even more preferably 3% by weight or above. The upper limit value is preferably 10% by weight or below, more preferably 8% by weight, or below, and may also be 6% by weight or below.

<Spherical Particle>

The ink composition of this invention preferably contains 0.01 to 1% by weight of a spherical particle having a particle size of 1.0 to 20.2 μm relative to the ink composition, and 0.1% by weight or less of a particle having a particle size exceeding 20.2 μm. The ink composition of this invention more preferably contains a particle having an average size of 3.0 to 17.5 μm, and, relative to the ink composition, contains 0.01 to 1% by weight of a spherical particle having a particle size of 1.0 to 20.2 μm, and 0.1% by weight or less of a particle having a particle size exceeding 20.2 μm.

The spherical particle will further be detailed below.

The particle used in this invention is spherical. By adding such particle to the ink composition, not only the offset becomes avoidable when the printed matters are successively stacked immediately after printing, but also the printed matter will be sampled more easily for inspection during printing.

In this invention, "spherical" is defined by an average sphericity of 0.85 or larger. The average sphericity is determined as below. One hundred particles are observed under an optical microscope to find sphericity values (=minor axis/major axis), that is, the ratios of the longest axes (major axes) and the shortest axes (minor axes) which pass near the center of the particle, and the arithmetic mean of the values is determined. The average sphericity is preferably 0.9, and more preferably 0.95.

In the ink composition of this invention, the amount of mixing of the spherical particle, when mixed, is preferably 0.01 to 1% by weight relative to the ink composition. The lower limit value of the amount of mixing of the spherical particle is preferably 0.05% by weight or more relative to the ink composition, and more preferably 0.08% by weight or more. The upper limit value is preferably 0.5% by weight or less relative to the ink composition, more preferably 0.4% by weight or less, even more preferably 0.35% by weight or less, and particularly 0.3% by weight or less. The amount of mixing of the spherical particle exceeding 1% by weight may however degrade the glossiness in printing, or may cause transfer failure of the ink composition to paper.

The thickness of an ink film in offset printing is typically 1 μm or around. Particles having a diameter of smaller than 1 μm may therefore be buried in the ink layer. Meanwhile, the particle size exceeding 20 μm may induce "piling", which means piling-up of the particle on the rollers or a rubber blanket, when the ink is transferred from an ink pot via a plurality of rollers to paper. Since the piling degrades the quality of printed image, so that addition of particles having particle sizes exceeding 20 μm is not preferable.

The spherical particle used in this invention preferably has a particle size of 1 to 20.2 μm. The lower limit value of the particle size of spherical particle preferably exceeds 3.0 μm, and more preferably exceeds 5.0 μm. The upper limit value of the particle size of spherical particle is preferably 15.6 μm or smaller. The content of particles larger than 20.2 μm in the ink composition of this invention is preferably 0.1% by weight less, and more preferably 0.01% by weight or less. The average particle size is preferably 3.0 to 17.5 μm, more preferably 3.0 to 15.6 μm, even more preferably 5.0 to 11.1 μm, and particularly 5.0 to 10.0 μm.

The particle size of the particle used in this invention is measured by the laser diffraction/scattering method using MT3000 from. Nikkiso Co., Ltd., in the form of dispersion in water.

The spherical particle employable in this invention is preferably any of resin-based particles, more preferably any of an olefinic particle, a styrene-based particle, a phenolic particle, a silicone-based particle, a urethane-based particle and a (meth)acrylic particle.

The particles employable in this invention are exemplified by those commercially available, which include (meth) acrylic particles typically marketed by Sekisui Plastics Co., Ltd. under the trade names of Techpolymer SSX-103, SSX-105, SSX-108, SSX-110, SSX-115, MBX-5, MBX-8, MBX-12, MB20X-5, MB30X-5 and MB30X-8. Also particles other than (meth)acrylic particle will do. Such particles include silicone-based particles available from Nikko Rica Corporation under the trade names of MSP-AS04, MSP-TS04, MSP-AK06 and MSP-TK04; polyethylene-based spherical particle available from Sumitomo Seika Chemicals Co., Ltd, under the trade name of Flo-Beads LE-1080; styrene-based spherical particle available from Soken Chemical & Engineering Co., Ltd. under the trade name of Chemisnow SX-500; and urethane-based particle available from Linden Co., Ltd, under the trade name of EPU-40. Only a single species of these particles may be used, or two or more species thereof may be used in combination.

When the spherical particle employed in this invention is added, it is preferable to disperse the colorant into the varnish and to knead the mixture as in the conventional method of manufacturing the ink composition, and then to add the particle into the ink.

<Colorant>

The ink composition of this invention includes not only color ink compositions, but also transparent or semi-transparent overprint varnish (may occasionally be abbreviated as "OP varnish", hereinafter). For the color ink composition, the colorant may be either dye or pigment, where the pigment, is typical. The pigment may be either organic pigment or inorganic pigment. The inorganic pigment is exemplified by chrome yellow, zinc yellow, Prussian blue, barium sulfate, cadmium red, titanium oxide, zinc white, alumina white, calcium carbonate, ultramarine blue, carbon black, graphite, and aluminum powder. The organic pigment is exemplified by azo-based, phthalocyanine-based, quinacridone-based, anthraquinone-based and dioxazine-based pigments.

Only a single species of colorant may be used, or two or more species thereof may be used in combination.

The lower limit value of the amount of mixing of the colorant, when mixed, in the ink composition of this invention is preferably 5% by weight or above and more preferably 10% by weight or above, meanwhile the upper limit value is preferably 55% by weight or below, more preferably 35% by weight or below, and even more preferably 30% by weight or below.

The color ink composition is basically available in four colors of yellow, magenta, cyan and key (black), which are respectively overlaid to give a variety of colors. Since these four colors, called "process color", however reduce vividness of color when overlaid, there are some fine color ink compositions having intermediate colors of purple, green and orange, which are included in the ink composition in this invention. The OP varnish is used for coating the printed surface for the purpose of glossing or matting the printed surface, or protecting the printed surface to give wear resistance, <Binder Resin>

The ink composition of this invention typically contains a binder resin. The binder resin is exemplified by polyester-based resins such as alkyd resin, rosin-modified alkyd resin, fatty acid-modified alkyd resin, petroleum resin-modified alkyd resin, urethane resin-modified alkyd resin, epoxy resin-modified alkyd resin, and unsaturated polyester resin; phenolic resins such as phenol resin, rosin-modified phenol resin, fatty acid-modified phenolic resin, petroleum, resin-modified rosin phenolic resin, alkyd resin-modified rosin phenolic resin, urethane resin-modified rosin phenolic resin, and epoxy resin-modified rosin phenolic resin; petroleum-based resins such as petroleum resin, rosin-modified petroleum resin and fatty acid-modified petroleum resin; amino-based resins such as urea resin, melamine resin, and benzoguanamine resin; naturally derived rosin-based resins such as rosin, fatty acid-modified rosin, polyhydric alcohol-modified rosin, alkyd resin-modified rosin, and petroleum, resin-modified rosin; cellulosic resins such as cellulose acetate and nitrocellulose; and cyclized rubber, where preferable examples include polyester-based resin and phenolic resin, more preferable examples include rosin-modified phenol resin and fatty acid-modified alkyd resin, and even more preferable examples include rosin-modified phenol resin.

Only a single species of binder resin may be used, or two or more species thereof may be used in combination.

The lower limit value of the amount of mixing of the binder resin in the ink composition of this invention is preferably 20% by weight or above, more preferably 23% by weight or above, and even more preferably 25% by weight or above, meanwhile the upper limit value is preferably 40% by weight or below, more preferably 37% by weight or below, and even more preferably 35% by weight or below of the ink composition.

<Drying Oil>

The ink composition of this invention typically contains a drying oil. The drying oil refers to an oil gradually oxidized in the air to be solidified. In this invention, the drying oil preferably has an iodine value of 100 or larger. The drying oil is exemplified by plant oils such as soybean oil, recycled soybean oil, rapeseed oil, coconut oil, hemp seed oil, linseed oil, olive oil, kaya (Japanese torreya nuts) oil, tung oil, poppy seed oil, sesame oil, safflower oil, rice bran oil, palm oil, castor oil, dehydrated castor oil, sunflower oil, cottonseed oil, and tall oil; and animal oils such as beef tallow and lard, wherein plant oils are preferable, and soybean oil, linseed oil, tung oil and rice bran oil are more preferable.

Only a single species of drying oil may be used, or two or more species thereof may be used in combination.

The lower limit value of the amount of mixing of the drying-oil in the ink composition of this invention is preferably 10% by weight or above of the ink composition, more preferably 12% by weight or above, and even more preferably 15% by weight or above, meanwhile the upper limit value is preferably 40% by weight or below of the ink composition, more preferably 35% by weight or below, and even more preferably 20% by weight or below.

<Solvent>

The ink composition of this invention typically contains a solvent. The solvent is preferably at least one species selected from the group consisting of petroleum solvents and plant-based solvents.

The petroleum solvents include aromatic solvents and aliphatic solvents, wherein the aliphatic solvents, also called mineral oil, are more popular in Japan since they are preferred in view of environmental measures. Among the petroleum solvents, the petroleum solvents having boiling points of 240 to 360° C. are preferred, and particularly for those intended for use in sheetfed ink composition, solvents having boiling points of 280 to 360° C. are preferably used. Commercially available solvents include Solvent AF-4, Solvent AF-5, Solvent AF-6 and Solvent AF-7 (all from JX Nippon Oil & Energy-Corporation).

The plant-based solvents are exemplified by ester compounds of fatty acids obtained from plant oils. The esters include methyl ester, n-butyl ester, i-butyl ester, n-octyl ester, 2-ethylhexyl ester, mono to triesters of trimethylolpropane, mono to tetraesters of pentaerythritol, and mono to hexaesters of dipentaerythritol. The plant oils are synonymous to those described under the title of "Drying Oil", defined by the same preferable ranges.

Only a single species of petroleum solvent or plant-based solvent may be used, or two or more species thereof may be used in combination.

The amount of mixing of the solvent in the ink composition of this invention is preferably 15 to 40% by weight of the ink composition, and more preferably 20 to 30% by weight.

<Dryer>

The ink composition of this invention may contain a dryer. The dryer is also referred to as drying accelerator, and is preferably a metal dryer.

The metal dryer is typically any of metal naphthenates and metal octylate, wherein the metal used therefor is exemplified by cobalt, manganese, zinc, iron, zirconium and calcium. For more improved dryability, also a peroxide compound may be added.

Only a single species of metal dryer may be used, or two or more species thereof may be used in combination.

The amount of mixing of the metal dryer, when mixed, in the ink composition of this invention is preferably 0.1 to 3% by weight of the ink composition, and more preferably 0.5 to 1.5% by weight. When the peroxide compound is used, the content thereof is preferably 0.01 to 1% by weight, and more preferably 0.05 to 0.5% by weight.

<Wax>

The ink composition of this invention may be blended with wax. Such wax is preferably used as an auxiliary for strengthening the film formed on the printed matter using the ink composition. The wax is exemplified by polyethylene, polypropylene, paraffin, microcrystalline wax, carnauba wax, beeswax, and polytetrafluoroethylene, which may be used independently or as a mixture of two or more species. The wax may be used in the form of powder to be kneaded into the ink, or in the formed of wax compound with a good workability. The amount of mixing of the wax, when mixed, is preferably 0.1 to 5% by weight relative to the ink composition, and more preferably 0.5 to 4% by weight.

<Other Additives>

Besides those described above, the ink composition of this invention may optionally be blended with any of additives such as gelating agent, pigment disperser, anti-skinning agent, antioxidant, abrasion resistance improver, and surfactant. Only a single species of these additives may be used, or two or more species thereof may be used in combination.

Preferred Embodiments of Ink Composition

Preferred embodiments of the ink composition of this invention will be described below. Note this invention is of course not limited to these embodiments.

<<Ink Composition (1)>>

A first embodiment of the ink composition of this invention contains 1 to 10% by weight of the (meth)acrylic resin, 20 to 35% by weight of the binder resin, 10 to 40% by weight of the drying oil, 15 to 40% by weight of the solvent (preferably petroleum solvent), 0.01 to 3% by weight of the dryer, and 0.1 to 5% by weight (preferably 0.1 to 3% by weight) of the wax.

The ink composition more preferably contains 2 to 6% by weight of the (meth)acrylic resin, 25 to 30% by weight of the binder resin, 15 to 35% by weight of the drying oil, 20 to 30% by weight of the solvent (preferably petroleum solvent), 0.5 to 1.5% by weight of the dryer, and 0.5 to 4% by weight (preferably 0.5 to 2% by weight) of the wax.

The content of the colorant, when contained, is preferably 0 to 55% by weight, and more preferably 10 to 35% by weight. In a more preferred embodiment, the amount of mixing of components other than the above-described components is preferably 1% by weight or less of the ink composition.

<<Ink Composition (2)>>

A second embodiment of the ink composition of this invention contains 20 to 45% by weight of the binder resin, 10 to 45% by weight of the drying oil, 15 to 45% by weight of the solvent (preferably petroleum, solvent), 0.01 to 3% by weight of the dryer, 0.1 to 5% by weight (preferably 0.1 to 3% by weight) of the wax, and 0.01 to 1% by weight of the spherical particle, wherein the amount of mixing of the particle having a particle size exceeding 20.2 μm is 0.1% by weight or less.

The ink composition preferably contains 25 to 35% by weight of the binder resin, 15 to 35% by weight of the drying oil, 20 to 30% by weight of solvent (preferably, petroleum solvent), 0.5 to 1.5% by weight of the dryer, 0.5 to 4% by weight (preferably 0.5 to 2% by weight) of the wax, and 0.05 to 0.5% by weight of the spherical particle having a particle size of 1.0 to 20.2 μm, wherein the amount of mixing of the particle having a particle size exceeding 20.2 μm is 0.1% by weight or less.

The content of the colorant, when contained, is preferably 0 to 55% by weight, and more preferably 10 to 35% by weight. In a more preferable embodiment, the amount of mixing of component(s) other than those described above is 1% by weight or less of the ink composition.

<<Ink Composition (3)>>

A third embodiment of the ink composition of this invention contains 1 to 10% by weight of the (meth)acrylic resin, 20 to 35% by weight of the binder resin, 10 to 40% by weight of the drying oil, 15 to 40% by weight of the solvent (preferably, petroleum solvent), 0.01 to 3% by weight of the dryer, 0.1 to 5% by weight (preferably, 0.1 to 3% by weight) of the wax and 0.01 to 1% by weight of the spherical particle, wherein the amount of mixing of the particle having a particle size exceeding 20.2 μm is 0.1% by weight or less.

The ink composition preferably contains 2 to 6% by weight of the (meth)acrylic resin, 25 to 30% by weight of the binder resin, 15 to 35% by weight of the drying oil, 20 to 30% by weight of the solvent (preferably, petroleum solvent), 0.5 to 1.5% by weight of the dryer, 0.5 to 4% by weight (preferably, 0.5 to 2% by weight) of the wax, and, 0.05 to 0.5% by weight of the spherical particle having a particle size of 1.0 to 20.2 μm, wherein the amount of mixing of the particle having a particle size exceeding 20.2 μm is 0.1% by weight or less.

The content of the colorant, when contained, is preferably 0 to 55% by weight, and more preferably 10 to 35% by weight. In a more preferable embodiment, the amount of mixing of component (s) other than those described above is 1% by weight or less of the ink composition.

<Method of Manufacturing Ink Compositions>

Method of manufacturing the ink composition of this invention may, for example, be any of known methods without special limitation. In an exemplary process, a binder resin such as rosin-modified phenol resin, a drying oil and its processed oil, a petroleum solvent and so forth are heated at 180 to 250° C. for one to two hours, to prepare a varnish. The thus obtained varnish is then added with a colorant such as pigment, a solvent (typically, petroleum solvent or plant-based solvent) and an additive, then milled and dispersed using a bead mill or three-roll mill, and adjusted to a proper viscosity with solvent or the like. The offset ink or OP varnish may thus be manufactured.

The ink composition of this invention may be applicable to a variety of printing systems, and particularly preferably to a planographic system. The ink composition of this invention is suitable for offset printing. In this invention, printing preferably takes place in an environment at 10 to 40° C.

Printing paper used for printing with the ink composition of this invention is selectable depending on the printing systems. Note that the printing paper in the context of this specification conceptually encompasses not only those made of paper, but also those made of materials other than paper.

EXAMPLE

This invention will now be detailed below referring to Examples, without limiting the scope of this invention. In the descriptions of Example of Manufacture below, "part(s)" and "%" shall represent "parts by weight" and "% by weight", respectively, unless otherwise specifically noted.

Synthesis Example

Synthesis Example 1 of (Meth)Acrylic Resin

In a glass reactor equipped with a mechanical stirrer, a thermometer, a condenser and a dry nitrogen gas feeding device, placed were isobornyl methacrylate (99 parts), methacrylic acid (1 part), azobis(methylbutyronitrile) (5 parts), and Solvent AF-5 (from JX Nippon Oil & Energy Corporation) (150 parts), the content was heated under a dry nitrogen gas flow up to 120° C. over 30 minutes, and was further kept at 120° C. for 3 hours, to obtain (meth)acrylic resin solution (1) having a concentration of 40% by weight on a solid basis. The glass transition temperature and the weight-average molecular weight of the obtained (meth) acrylic resin were summarized in Table 1.

Synthesis Examples 2 to 5 of (Meth)Acrylic Resin (Meth) acrylic resin solutions (2) to (5) were obtained in the same way as in Synthesis Example 1, except that the amounts of consumption of isobornyl methacrylate, methacrylic acid, azobis(methylbutyronitrile), and Solvent AF-5 were respectively changed to the amounts summarized in Table 1 below. The glass transition temperature, the weight-average molecular weight and the solid concentration of the obtained (meth)acrylic resin were summarized in Table 1.

Synthesis Example 6 of (Meth)Acrylic Resin

In the same reactor as used in Synthesis Example 1, placed were isobornyl methacrylate (80 parts), 2-ethylhexyl methacrylate (19 parts), methacrylic acid (1 part), azobis (methylbutyronitrile) (5 parts), and Solvent AF-5 (from JX Nippon Oil & Energy Corporation) (100 parts), and processed in the same way as in Synthesis Example 1, to obtain (meth)acrylic resin solution (6), The glass transition temperature, the weight-average molecular weight and the solid concentration of the obtained (meth)acrylic resin were summarized in Table 1.

Synthesis Example 7 of (Meth)Acrylic Resin

In the same glass reactor as used in Synthesis Example 1, placed were isobornyl methacrylate (78 parts), 2-ethylhexyl acrylate (21 parts), methacrylic acid (1 part), azobis(methylbutyronitrile) (2.5 parts), and Solvent AF-5 (from JX Nippon Oil & Energy Corporation) (150 parts), and processed in the same way as in Synthesis Example 1, to obtain (meth)acrylic resin solution (7), The glass transition temperature, the weight-average molecular weight and the solid concentration of the obtained (meth)acrylic resin were summarized in Table 1.

Synthesis Example 8 of (Meth)Acrylic Resin

In the same glass reactor as used in Synthesis Example 1, placed were t-butylcyclohexyl methacrylate (90 parts), n-butyl methacrylate (10 parts), azoabis(methylbutyronitrile) (2.5 parts), and Solvent AF-5 (150 parts), and processed in the same way as in Synthesis Example 1, to obtain (meth) acrylic resin solution (8). The glass transition temperature, the weight-average molecular weight and the solid concentration of the obtained (meth)acrylic resin were summarized in Table 1.

Synthesis Example 9 of (Meth)Acrylic Resin

In the same glass reactor as used in Synthesis Example 1, placed were dicyclopentanyl methacrylate (80 parts), 2-ethylhexyl methacrylate (20 parts), azobis(methylbutyronitrile) (2.5 parts), and Solvent AF-5 (150 parts), and processed in the same way as in Synthesis Example 1, to obtain (meth) acrylic resin solution (9). The glass transition temperature, the weight-average molecular weight and the solid concentration of the obtained (meth) acrylic resin were summarized in Table 1.

Synthesis Example 10 of (Meth)Acrylic Resin

In the same glass reactor as used in Synthesis Example 1, placed were isobornyl methacrylate (99 parts), methacrylic acid (1 part), azobis(methylbutyronitrile) (1.5 parts), and Solvent AF-5 (230 parts), the content was heated under a dry nitrogen gas flow up to 90° C. over 30 minutes, and was further kept at 90° C. for 3 hours, to obtain (meth)acrylic resin solution (10) having a concentration of 30% by weight on a solid basis. The glass transition temperature and the weight-average molecular weight of the obtained (meth) acrylic resin were summarized in Table 1.

Synthesis Example 11 of (Meth)Acrylic Resin

In the same glass reactor as used in Synthesis Example 1, placed were isobornyl methacrylate (99 parts), methacrylic acid (1 part), azobis(methylbutyronitrile) (1 part), and Solvent AF-5 (230 parts), the content was heated under a dry nitrogen gas flow up to 90° C. over 30 minutes, and was further kept at 90° C. for 3 hours, to obtain (meth)acrylic resin solution (11) having a concentration of 30% by weight on a solid basis. The glass transition temperature and the weight-average molecular weight of the obtained (meth) acrylic resin were summarized in Table 1.

Synthesis Example 12 of (Meth)Acrylic Resin

In the same glass reactor as used in Synthesis Example 1, placed were isobornyl methacrylate (69 parts), styrene (30 parts), methacrylic acid (1 part), azobis(methylbutyronitrile) (1.5 parts), and Solvent AF-5 (105 parts), the content was heated under a dry nitrogen gas flow up to 90° C. over 30 minutes, and was further kept at 90° C. for 3 hours. Then 45 parts of i-butyl ester of soybean oil fatty acid (Tosolv-IB, from Toshin Yushi Co., Ltd.) was added, to obtain (meth) acrylic resin solution (12) having a concentration of 40% by weight on a solid basis. The glass transition temperature and the weight-average molecular weight of the obtained (meth) acrylic resin were summarized in Table 1.

Synthesis Example 13 of (Meth)Acrylic Resin

In the same glass reactor as used in Synthesis Example 1, placed were isobornyl methacrylate (99 parts), methacrylic acid (1 part), azobis (methylbutyronitrile) (0.5 parts), and Solvent AF-5 (230 parts), and processed in the same way as in Synthesis Example 1, to obtain (meth) acrylic resin solution (13). The glass transition temperature, the weight-average molecular weight and the solid concentration of the obtained (meth)acrylic resin were summarized in Table 1.

Synthesis Example 14 of (Meth)Acrylic Resin

In the same glass reactor as used in Synthesis Example 1, placed were isobornyl methacrylate (99 parts), methacrylic acid (1 part), azobis(methylbutyronitrile) (0.5 parts), and Solvent AF-5 (from JX Nippon Oil & Energy Corporation) (150 parts), the content was heated, under a dry nitrogen gas flow up to 100° C. over 30 minutes, and was further kept at 100° C. for 3 hours, then cooled, and Solvent AF-5 (75 parts) was added, at 80° C., to obtain (meth) acrylic resin solution (14) having a concentration of 30% by weight on a solid basis. The glass transition temperature and the weight-average molecular weight of the obtained (meth)acrylic resin were summarized in Table 1.

Comparative Synthesis A of (Meth)Acrylic Resin

In the same glass reactor as used in Synthesis Example 1, placed were isobornyl methacrylate (50 parts), 2-ethylhexyl methacrylate (50 parts), azobis(methylbutyronitrile) (3 parts), and Solvent AF-5 (from JX Nippon Oil & Energy Corporation) (150 parts), and processed in the same way as in Synthesis Example 1, to obtain (meth)acrylic resin solution (A). The glass transition temperature, the weight-average molecular weight, and the solid concentration of the obtained (meth)acrylic resin were summarized in Table 1. The obtained (meth) acrylic resin did not satisfy requirement (2) stating that "the glass transition temperature is 63 to 180° C.".

Comparative Synthesis B of (Meth)Acrylic Resin

In the same glass reactor as used in Synthesis Example 1, placed were isobornyl methacrylate (40 parts), n-butyl methacrylate (60 parts), azobis (methylbutyronitrile) (5 parts), and Solvent AF-5 (from JX Nippon Oil & Energy Corporation) (150 parts), and processed in the same way as in Synthesis Example 1, to obtain (meth)acrylic resin solution (B), The glass transition temperature, the weight-average molecular weight, and the solid, concentration of the obtained (meth)acrylic resin were summarized in Table 1. The obtained (meth) acrylic resin did not satisfy requirement (2) stating that "the glass transition temperature is 63 to 180° C.".

Comparative Synthesis C of (Meth)Acrylic Resin

In the same glass reactor as used in Synthesis Example 1, placed were methyl methacrylate (80 parts), 2-ethylhexyl methacrylate (20 parts), azobis(methylbutyronitrile) (2.5 parts), and Solvent AF-5 (from JX Nippon Oil & Energy Corporation) (150 parts), and processed in the same way as in Synthesis Example 1, but failed to obtain the product as a solution, since a white solid deposited in the process of polymerization at 120° C. The glass transition temperature and the weight-average molecular weight of the obtained (meth)acrylic resin were summarized in Table 1. The obtained, (meth) acrylic resin did not satisfy requirement (1) stating that "containing at least 40% by weight or more of acryl monomer unit having a straight-chain, branched or cyclic alkyl group having 4 or more carbon atoms".

Comparative Synthesis D of (Meth)Acrylic Resin

In the same glass reactor as used in Synthesis Example 1, placed were isobornyl methacrylate (99 parts), methacrylic acid (1 part), azobis(methylbutyronitrile) (0.5 parts), and Solvent AF-5 (from JX Nippon Oil & Energy Corporation) (150 parts), the content was heated under a dry nitrogen gas flow up to 90° C. over 30 minutes, and was further kept at 90° C. for 3 hours, then cooled, and Solvent AF-5 (75 parts) was added at 80° C., to obtain (meth)acrylic resin solution (D) having a concentration of 30% by weight on a solid basis. The glass transition temperature and the weight-average molecular weight of the obtained, (meth) acrylic resin were summarized in Table 1.

TABLE 1

|  | Unit | Synthesis Example1 | Synthesis Example2 | Synthesis Example3 | Synthesis Example4 | Synthesis Example5 |
| --- | --- | --- | --- | --- | --- | --- |
| IBMA | parts by weight | 99 | 99 | 99 | 99 | 98 |
| MAA | parts by weight | 1 | 1 | 1 | 1 | 2 |
| DCPMA | parts by weight | | | | | |
| t-BuCHMA | parts by weight | | | | | |
| EHMA | parts by weight | | | | | |
| n-BuMA | parts by weight | | | | | |
| SM | parts by weight | | | | | |
| MMA | parts by weight | | | | | |
| AMBN | parts by weight | 5 | 2.5 | 1.5 | 1 | 5 |
| AF5 | parts by weight | 150 | 230 | 230 | 230 | 150 |
| Tosolv-IB | parts by weight | | | | | |
| Solid concentration | wt % | 40 | 30 | 30 | 30 | 40 |
| Reaction temperature | ° C. | 120° C. | 120° C. | 120° C. | 120° C. | 120° C. |
| Tg | ° C. | 155 | 155 | 155 | 155 | 154 |
| Mw | | 4,000 | 8,000 | 15,000 | 19,000 | 4,800 |

TABLE 1-continued

|  | Synthesis Example6 | Synthesis Example7 | Synthesis Example8 | Synthesis Example9 | Synthesis Example10 |
|---|---|---|---|---|---|
| IBMA | 80 | 78 |  |  | 99 |
| MAA | 1 | 1 |  |  | 1 |
| DCPMA |  |  |  | 80 |  |
| t-BuCHMA |  |  | 90 |  |  |
| EHMA | 19 | 21 |  | 20 |  |
| n-BuMA |  |  | 10 |  |  |
| SM |  |  |  |  |  |
| MMA |  |  |  |  |  |
| AMBN | 5 | 2.5 | 2.5 | 2.5 | 1.5 |
| AF5 | 100 | 150 | 150 | 150 | 230 |
| Tosolv-IB |  |  |  |  |  |
| Solid concentration | 40 | 40 | 40 | 40 | 30 |
| Reaction temperature | 120° C. | 120° C. | 120° C. | 120° C. | 90° C. |
| Tg | 109 | 64 | 111 | 120 | 155 |
| Mw | 3,500 | 8,200 | 21,000 | 19,000 | 22,000 |

|  | Unit | Synthesis Example11 | Synthesis Example12 | Synthesis Example13 | Synthesis Example14 | Comparative Synthesis A | Comparative Synthesis B | Comparative Synthesis C | Comparative Synthesis D |
|---|---|---|---|---|---|---|---|---|---|
| IBMA | parts by weight | 99 | 69 | 99 | 99 | 50 | 40 |  | 99 |
| MAA | parts by weight |  | 1 | 1 | 1 |  |  |  | 1 |
| DCPMA | parts by weight |  |  |  |  |  |  |  |  |
| t-BuCHMA | parts by weight |  |  |  |  |  |  |  |  |
| EHMA | parts by weight |  |  |  |  | 50 |  | 20 |  |
| n-BuMA | parts by weight |  |  |  |  |  | 60 |  |  |
| SM | parts by weight |  | 30 |  |  |  |  |  |  |
| MMA | parts by weight |  |  |  |  |  |  | 80 |  |
| AMBN | parts by weight | 1 | 1.5 | 0.5 | 0.5 | 3 | 5 | 2.5 | 0.5 |
| AF5 | parts by weight | 230 | 105 | 230 | 225 | 150 | 150 | 150 | 225 |
| Tosolv-IB | parts by weight |  | 45 |  |  |  |  |  |  |
| Solid concentration | wt % | 30 | 40 | 30 | 30 | 40 | 40 |  | 30 |
| Reaction temperature | ° C. | 90° C. | 90° C. | 120° C. | 100° C. | 120° C. | 120° C. | 120° C. | 90° C. |
| Tg | ° C. | 155 | 138 | 155 | 155 | 53 | 62 | 75 | 155 |
| Mw |  | 31,000 | 20,000 | 51,000 | 60,000 | 8,500 | 24,000 | 19,000 | 95,000 |

IBMA: isobornyl methacrylate
MAA: methacrylic acid
DCPMA: dicyclopentanyl methacrylate
t-BuCHMA: t-butylcyclohexyl methacrylate
EHMA: 2-ethylhexyl methacrylate
n-BuMA: n-butyl methacrylate
SM: styrene
MMA: methyl methacrylate
AMBN: azobis(methylbutyronitrile)
AF5: Solvent AF-5
Tosolv-IB: i-butyl ester of soybean oil fatty acid
Tg: Glass transition temperature (° C.) calculated from the aforementioned Equation (1)
Mw: Weight-average molecular weight measured as described above.
Solid concentration: Calculated from the amount of residue remained after drying in a hot air circulation dryer at 150° C. for 1 h to completely remove the solvent.

<<Manufacture of Varnish for Offset Printing>>

Varnish A

Into a one-liter, three-necked flask equipped with a stirrer and a thermometer, placed were Tespol 1365 (from Harima Chemicals Group, Inc.) as a rosin-modified phenol resin (42 parts), refined soybean oil (from Summit Oil Mill Co., Ltd.) (25 parts), and Solvent AF-6 (from JX Nippon Oil & Energy Corporation) (2.0 parts), the content was heated to 200° C., kept, at that temperature for one hour for dissolution, then added with Solvent AF-6 (12 parts), and ALCH (from Kawaken Fine Chemicals Co., Ltd.) as a gelating agent (1 part), stirred under heating at 180° C. for one hour, to obtain Varnish A.

Varnish B

Into a one-liter, three-necked flask equipped with a stirrer and a thermometer, placed were Tespol 1366 (from. Harima Chemicals Group, Inc.) as a rosin-modified phenol resin (40 parts), LX-005M (Dia Var Chemical Company) as an alkyd resin (10 parts), soybean sirasimeyu oil (from Summit Oil Mill Co., Ltd.) (25 parts), and Solvent AF-6 (from JX Nippon Oil & Energy Corporation) (15 parts), the content was heated to 200° C., kept at that temperature for one hour for dissolution, then added with Solvent AF-6 (9 parts), and ALCH (from Kawaken Fine Chemicals Co., Ltd.) as a gelating agent (1 part), stirred under heating at 180° C. for one hour, to obtain Varnish B.

Varnish C

Into a one-liter, three-necked, flask equipped with a stirrer and a thermometer, placed were KG-823-1 (from Arakawa Chemical Industries, Ltd.) as a rosin-modified phenol resin (45 parts), refined soybean oil (from Summit Oil Mill Co., Ltd.) (20 parts), and Solvent AF-6 (from JX Nippon Oil & Energy Corporation) (12 parts), the content was heated to 200° C., kept at that temperature for one hour for dissolution, then added with tung oil (from Kaneda Co., Ltd.) (10 parts), Solvent. AF-6 (1.2 parts), and ALCH (from Kawaken Fine Chemicals Co., Ltd.) as a gelating agent (1 part), the content was stirred under heating at 180° C. for one hour, to obtain Varnish C. Compositions of Varnishes A, B and C were summarized in Table 2.

TABLE 2

|  |  | Varnish | | |
|---|---|---|---|---|
|  |  | A | B | C |
| Binder resin | Rosin-modified phenolic resin | 42 | 40 | 45 |
|  | Alkyd resin |  | 10 |  |
| Drying oil | Refined soybean oil | 25 | 25 | 20 |
|  | Tung oil |  |  | 10 |
| Petroleum solvent | Solvent AF-6 | 32 | 24 | 24 |
| Gelating agent | ALCH | 1 | 1 | 1 |
|  | Total | 100 | 100 | 100 |

In Table 2, values are given in "part(s) by weight".

<<Manufacture of Acrylic Resin-Containing Ink Composition for Offset Printing>>

Examples 1 to 14

Varnish A (60 parts) obtained in Example of Manufacture of varnish and phthalocyanine blue (A-721-EP, from. Dainichiseika Color & Chemicals Mfg. Co., Ltd.) (18 parts) were mixed, and the mixture was successively milled using a bead mill and a three-roll mill, to obtain each ink base. Each ink base was added with a polyethylene wax (MC-850, from Morimura Chemicals, Ltd.) (5 parts in a compound basis, itemized by 1.5 parts of polyethylene, 0.15 parts of binder resin, 3.1 parts of drying oil, and 0.25 parts of petroleum solvent, the same will apply hereinafter), a metal dryer (N dryer, from Ninon Kagaku Sangyo Co., Ltd.) (1 part), the (meth)acrylic resin of any one of Synthesis Example 1 to 15 (10 parts on a solution basis), and Solvent AF-6 (6 parts), and the content was stirred to obtain each of ink compositions for offset printing of Examples 1 to 14.

Examples 15, 17 and 19

Varnish A (65 parts) obtained in Example of Manufacture of varnish and phthalocyanine blue (A-721-EP, from Dainichiseika Color & Chemicals Mfg. Co., Ltd.) (18 parts) were mixed, and the mixture was successively milled using a bead mill and a three-roll mill, to obtain each ink base. Each ink base was added with a polyethylene wax (MC-850, from Morimura Chemicals, Ltd.) (5 parts), a metal dryer (N dryer, from Nihon Kagaku Sangyo Co., Ltd.) (1 part), the (meth)acrylic resin of any one of Synthesis Example 1, 2 and 8 (5 parts on a solution basis), and Solvent AF-6 (6 parts), and the content was stirred to obtain each of ink compositions for offset printing of Examples 15, 17 and 19.

Examples 16, 18 and 20

Varnish A (55 parts) obtained in Example of Manufacture of varnish and phthalocyanine blue (A-721-EP, from Dainichiseika Color & Chemicals Mfg. Co., Ltd.) (18 parts) were mixed, and the mixture was successively milled using a bead mill and a three-roll mill, to obtain each ink base. Each ink base was added with a polyethylene wax (MC-850, from Morimura Chemicals, Ltd.) (5 parts), a metal dryer (N dryer, from Nihon Kagaku Sangyo Co., Ltd.) (1 part), the (meth)acrylic resin of any one of Synthesis Example 1, 2 and 8 (15 parts on a solution basis), and Solvent AF-6 (6 parts), and the content was stirred to obtain each of ink compositions for offset printing of Examples 16, 18 and 20.

Comparative Examples 1 to 3

Varnish A (60 parts) obtained in Example of Manufacture of varnish and phthalocyanine blue (A-721-EP, from Dainichiseika Color & Chemicals Mfg. Co., Ltd.) (18 parts) were mixed, and the mixture was successively milled using a bead mill and a three-roll mill, to obtain each ink base. Each ink base was added with a polyethylene wax (MC-850, from Morimura Chemicals, Ltd.) (5 parts), a metal dryer (N dryer, from Nihon Kagaku Sangyo Co., Ltd.) (1 part), the (meth)acrylic resin of any one of Synthesis Example A, B and D (10 parts on a solution basis), and Solvent AF-6 (6 parts), and the content was stirred to obtain each of ink compositions for offset printing of Comparative Examples 1 to 3.

Comparative Examples 4 and 6

Varnish A (65 parts) obtained in Example of Manufacture of varnish and phthalocyanine blue (A-721-EP, from Dainichiseika Color & Chemicals Mfg. Co., Ltd.) (18 parts) were mixed, and the mixture was successively milled using a bead mill and a three-roll mill, to obtain each ink base. Each ink base was added with a polyethylene wax (MC-850, from Morimura Chemicals, Ltd.) (5 parts), a metal dryer (N dryer, from Nihon Kagaku Sangyo Co., Ltd.) (1 part), the (meth)acrylic resin of either of Synthesis Example A and B (5 parts on a solution basis), and Solvent AF-6 (6 parts), and the content was stirred to obtain each of ink compositions for offset printing of Comparative Examples 4 and 6.

Comparative Examples 5 and 7

Varnish A (55 parts) obtained in Example of Manufacture of varnish and phthalocyanine blue (A-721-EP, from Dainichiseika Color & Chemicals Mfg. Co., Ltd.) (18 parts) were mixed, and the mixture was successively milled using a bead mill and a three-roll mill, to obtain each ink base. Each ink base was added with a polyethylene wax (MC-850, from Morimura Chemicals, Ltd.) (5 parts), a metal dryer (N dryer, from Nihon Kagaku Sangyo Co., Ltd.) (1 part), the (meth)acrylic resin of either of Synthesis Example A and B (15 parts on a solution basis), and Solvent AF-6 (6 parts), and the content was stirred to obtain each of ink compositions for offset printing of Comparative Examples 5 and 7.

<<Manufacture of Particle-Containing ink Composition for Offset Printing>>

Particle size distribution on a volume basis of the particles, used in Examples below, were measured.

TABLE 3

|  | Spherical particle A | Spherical particle B | Spherical particle C | Spherical particle D | Spherical particle E | Spherical particle F | Spherical particle G |
|---|---|---|---|---|---|---|---|
| Ratio of under 1 μm fraction | 0 | 0 | 0 | 0 | 2.3 | 0 | 0 |

TABLE 3-continued

| | | | | | | | |
|---|---|---|---|---|---|---|---|
| Ratio of under 3.0 μm fraction | 0 | 0 | 0 | 0 | 11.1 | 1.3 | 2.5 |
| Ratio of under 5.0 μm fraction | 8 | 0 | 5.1 | 0 | 19.9 | 68.1 | 13.2 |
| Ratio of under 15.6 μm fraction | 100 | 91.5 | 99.7 | 0.4 | 97 | 100 | 99.6 |
| Ratio of under 20.2 μm fraction | | 98.1 | 100 | 10.3 | 99.2 | | 100 |
| Ratio of under 26.2 μm fraction | | 99.6 | | 51.8 | 100 | | |
| Ratio of under 31.1 μm fraction | | 100 | | 77 | | | |
| Ratio of under 52.3 μm fraction | | | | 96.9 | | | |
| Ratio of under 148.0 μm fraction | | | | 100 | | | |
| Average sphericity | 0.98 | 0.98 | 0.97 | 0.98 | 0.97 | 0.97 | 0.98 |
| Average size | 6.5 | 11.1 | 6.9 | 25.9 | 7.6 | 4.6 | 6.6 |

| | Spherical particle H | Spherical particle I | Spherical particle J | Spherical particle K | Non-spherical particle |
|---|---|---|---|---|---|
| Ratio of under 1 μm fraction | 0 | 15.7 | 0 | 0 | 0 |
| Ratio of under 3.0 μm fraction | 0.3 | 99.4 | 0.2 | 0 | 1.2 |
| Ratio of under 5.0 μm fraction | 2.3 | 100 | 1.6 | 0 | 3.1 |
| Ratio of under 15.6 μm fraction | 48.6 | | 29.3 | 9.9 | 86 |
| Ratio of under 20.2 μm fraction | 86.1 | | 72.9 | 51.4 | 93.8 |
| Ratio of under 26.2 μm fraction | 96.9 | | 93 | 86.2 | 97.1 |
| Ratio of under 31.1 μm fraction | 98.8 | | 97.1 | 94.8 | 98.3 |
| Ratio of under 52.3 μm fraction | 100 | | 100 | 100 | 100 |
| Ratio of under 148.0 μm fraction | | | | | |
| Average sphericity | 0.98 | 0.98 | 0.98 | 0.98 | 0.69 |
| Average size | 15.7 | 1.3 | 17.5 | 20 | 10.1 |

The values of ratio of particles are given in "%".
Spherical particle A: acrylic resin SSX-105, from Sekisui Plastics Co., Ltd.
Spherical particle B: acrylic resin SSX-110, from Sekisui Plastics Co., Ltd.
Spherical particle C: acrylic resin SSX-108, from Sekisui Plastics Co., Ltd.
Spherical particle D: acrylic resin SSX-127, from Sekisui Plastics Co., Ltd.
Spherical particle E: acrylic resin MB30X-8, from Sekisui Plastics Co., Ltd.
Spherical particle F: styrene resin SX-500, from Soken Chemical & Engineering Co., Ltd.
Spherical particle G: silicone resin MSP-AK06, from Nikko Rica Corporation
Spherical particle H: acrylic resin SSX-115, from Sekisui Plastics Co., Ltd.
Spherical particle I: acrylic resin SSX-101, from Sekisui Plastics Co., Ltd.
Spherical particle J: acrylic resin SSX-115/SSX-120, from Sekisui Plastics Co., Ltd.
Spherical particle K: acrylic resin MZ-20HN, from Soken Chemical & Engineering Co., Ltd.
Non-spherical particle: starch AS-900, from Nikka Ltd.

The average particle size is the central value of volume distribution (median diameter).

Figure 2:
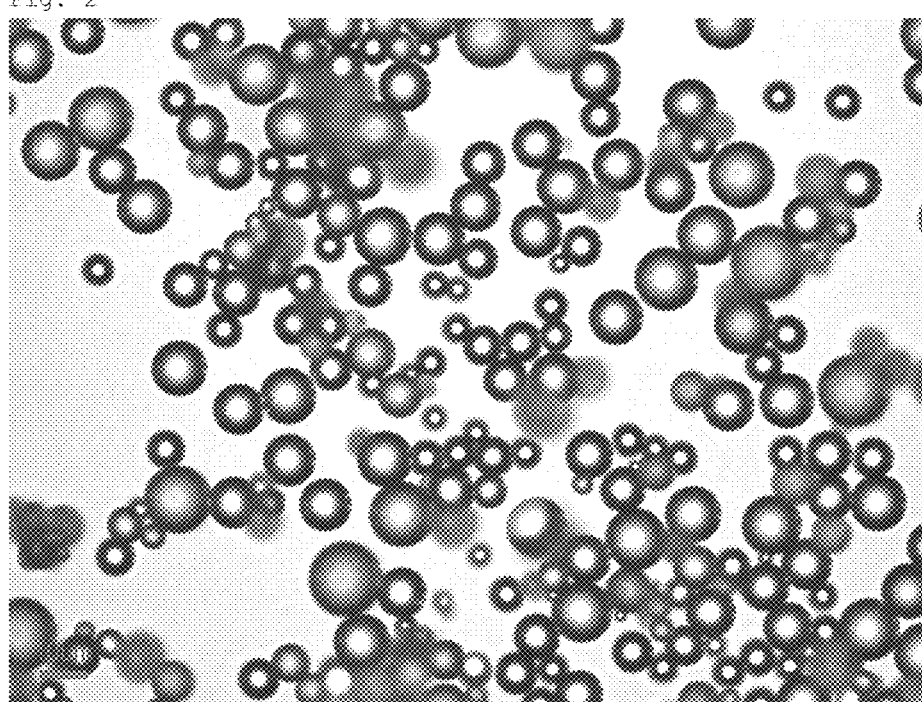
FIG. 2 A result of optical microscopic observation of a spherical particle used in Example of this invention.
Figure 3:
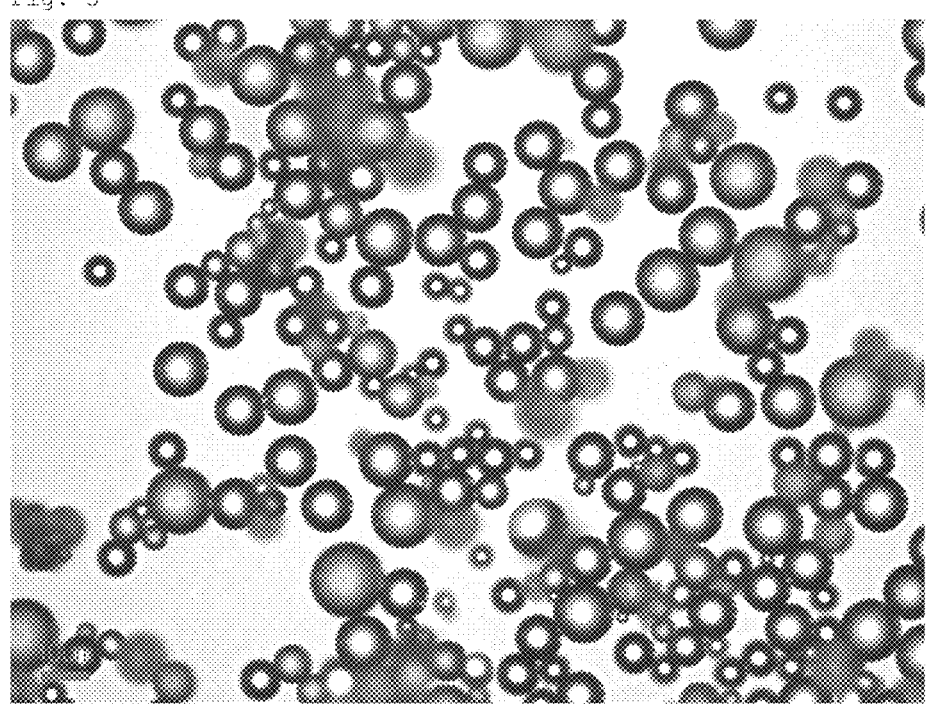
FIG. 3 A result of optical microscopic observation of a non-spherical particle used in Comparative Example of this invention.

FIG. 2 snows an optical micrograph of Spherical particle A, and FIG. 3 shows an optical micrograph of non-spherical particle.

Examples 21 and 22

Varnish A obtained in Example of Manufacture of varnish (70 parts) and phthalocyanine blue (A-721-EP, from Dainichiseika Color & Chemicals Mfg. Co., Ltd.) (18 parts) were mixed, and the mixture was successively milled using a bead mill and a three-roll mill, to obtain each ink base. Each ink base was added, with a polyethylene wax (MC-850, from Morimura Chemicals, Ltd.) (5 parts), a metal dryer (N dryer, from Nihon Kagaku Sangyo Co., Ltd.) (1 part), Spherical particle A or B (0.3 parts of either one), and Solvent AF-6 (5.7 parts), and the content was stirred to obtain each of ink compositions for offset printing of Examples 21 and 22.

Comparative Examples 8 and 9

Varnish A obtained in Example of Manufacture of varnish (65 parts) and phthalocyanine blue (A-721-EP, from Dainichiseika Color & Chemicals Mfg. Co., Ltd) (18 parts) were mixed, and the mixture was successively milled using a bead mill and a three-roll mill, to obtain each ink base. Each ink base was added with a polyethylene wax (MC-850, from Morimura Chemicals, Ltd.) (5 parts), a metal dryer (N dryer, from Ninon Kagaku Sangyo Co., Ltd.) (1 part), Spherical particle B or C (5 parts of either one), and Solvent AF-6 (6 parts), and the content was stirred to obtain each of ink compositions for offset printing of Comparative Examples 8 and 9.

<<Manufacture of Ink Composition for Offset Printing Containing Acrylic Resin and Particle>>

Examples 23 and 25

Varnish A obtained in Example of Manufacture of varnish (69.5 parts) and phthalocyanine blue (A-721-EP, from Dainichiseika Color & Chemicals Mfg. Co., Ltd.) (18 parts) were mixed, and the mixture was successively milled using a bead mill and a three-roll mill, to obtain each ink base. Each ink base was added with a polyethylene wax (MC-850, from Morimura Chemicals, Ltd.) (5 parts), a metal dryer (N dryer, from Ninon Kagaku Sangyo Co., Ltd.) (1 part), Spherical particle A or B (0.5 parts of either one), and Solvent AF-6 (6 parts), and the content was stirred to obtain each of ink compositions for offset printing of Examples 23 and 25.

Examples 24 and 26

Varnish A obtained in Example of Manufacture of varnish (69 parts) and phthalocyanine blue (A-721-EP, from Dainichiseika Color & Chemicals Mfg. Co., Ltd) (18 parts) were mixed, and the mixture was successively milled using a bead mill and a three-roll mill, to obtain each ink base. Each ink base was added with a polyethylene wax (MC-850, from Morimura Chemicals, Ltd.) (5 parts), a metal dryer (N dryer, from Ninon Kagaku Sangyo Co., Ltd.) (1 part), Spherical particle A or B (1 part of either one), and Solvent AF-6 (6 parts), and the content was stirred to obtain each of ink compositions for offset printing of Examples 24 and 26.

Examples 27, 31, 35, 39 and 43

Varnish A obtained, in Example of Manufacture of varnish (66 parts) and Disazo Yellow (Yellow 2606, from Dainichiseika Color & Chemicals Mfg. Co., Ltd.) (12 parts) were mixed, and the mixture was successively milled using a bead mill and a three-roll mill, to obtain each ink base. Each ink base was added with a polyethylene wax (MC-850, from Morimura Chemicals, Ltd.) (5 parts), a metal dryer (N dryer, from Nihon Kagaku Sangyo Co., Ltd.) (1 part), the (meth) acrylic resin of Synthesis Example 1 (10 parts on a solution basis), Spherical particle C, E, F, G or H (0.3 parts of any one of them), and Solvent AF-6 (5.7 parts), and the content was stirred to obtain each of ink compositions for offset printing of Examples 27, 31, 35, 39 and 43.

Examples 28, 32, 36, 40 and 44

Varnish A obtained in Example of Manufacture of varnish (60 parts) and Carmine 6B (6BC-474-2, from Sumika Color Co., Ltd.) (18 parts) were mixed, and the mixture was successively milled using a bead mill and a three-roll mill, to obtain each ink base. To each ink base, a polyethylene wax (MC-850, from. Morimura Chemicals, Ltd.) (5 parts), a metal dryer (N dryer, from Nihon Kagaku Sangyo Co., Ltd.) (1 part), the (meth) acrylic resin of Synthesis Example 1. (10 parts on a solution basis), Spherical particle C, E, F, G or H (0.3 parts of any one of them), and Solvent AF-6 (5.7 parts), and the content was stirred to obtain each of ink compositions for offset printing of Examples 28, 32, 36, 40 and 44.

Examples 29, 33, 37, 41 and 45

Varnish A obtained in Example of Manufacture of varnish (60 parts) and phthalocyanine blue (A-721-EP, from Dainichiseika Color & Chemicals Mfg. Co., Ltd.) (18 parts) were mixed, and the mixture was successively milled using a bead mill and a three-roll mill, to obtain each ink base. Each ink base was added with a polyethylene wax (MC-850, from Morimura Chemicals, Ltd.) (5 parts), a metal dryer (N dryer, from Nihon Kagaku Sangyo Co., Ltd.) (1 part), the (meth) acrylic resin of Synthesis Example 1 (10 parts on a solution basis), Spherical particle C, E, F, G or H (0.3 parts of any one of them), and Solvent AF-6 (5.7 parts), and the content was stirred to obtain each of ink compositions for offset printing of Examples 29, 33, 37, 41 and 45.

Examples 30, 34, 38, 42 and 46

Varnish B obtained in Example of Manufacture of varnish (54 parts), alkali blue toner (EB-18L, from Morimura Chemicals, Ltd.) (5 parts), and a carbon black (MA11, from Mitsubishi Chemical Corporation) (20 parts) were mixed, and the mixture was successively milled using a bead mill and a three-roll mill, to obtain each ink base. Each ink base was added with a polyethylene wax (MC-850, from Morimura Chemicals, Ltd.) (5 parts), a metal dryer (N dryer, from Ninon Kagaku Sangyo Co., Ltd.) (1 part), (meth) acrylic resin of Synthesis Example 1 (10 parts on a solution basis), spherical particle C, E, F, G or H (0.3 parts of any one of them), and Solvent AF-6 (4.7 parts), and the content was stirred to obtain each of ink compositions for offset printing of Examples 30, 34, 38, 42 and 46.

Example 47

Varnish A obtained in Example of Manufacture of varnish (66 parts) and Disazo Yellow (Yellow 2606, from Dainichiseika Color & Chemicals Mfg. Co., Ltd.) (12 parts) were mixed, and the mixture was successively milled using a bead mill and a three-roll mill, to obtain an ink base. The ink base was added with a polyethylene wax (MC-850, from Morimura Chemicals, Ltd.) (5 parts), a metal dryer (N dryer, from Nihon Kagaku Sangyo Co., Ltd.) (1 part), the (meth) acrylic resin of Synthesis Example 1 (10 parts on a solution basis), spherical particle J (0.24 parts), and Solvent AF-6 (5.76 parts), and the content was stirred to obtain an ink composition for offset printing of Example 47.

Example 48

Varnish A obtained in Example of Manufacture of varnish (60 parts) and Carmine 6B (6BC-474-2, from Sumika Color Co., Ltd.) (18 parts) were mixed, and the mixture was successively milled using a bead mill and a three-roll mill, to obtain an ink base. The ink base was added with a polyethylene wax (MC-850, from Morimura Chemicals, Ltd.) (5 parts), a metal dryer (N dryer, from Nihon Kagaku Sangyo Co., Ltd.) (1 part), the (meth)acrylic resin of Synthesis Example 1 (10 parts on a solution basis), Spherical particle J (0.24 parts), and Solvent AF-6 (5.76 parts), and the content was stirred to obtain an ink composition for offset printing of Example 48.

Example 49

Varnish A obtained in Example of Manufacture of varnish (60 parts) and phthalocyanine blue (A-721-EP, from Dainichiseika Color & Chemicals Mfg. Co., Ltd.) (18 parts) were mixed, and the mixture was successively milled using a bead mill and a three-roll mill, to obtain an ink base. The ink base was added with a polyethylene wax (MC-850, from Morimura Chemicals, Ltd.) (5 parts), a metal dryer (N dryer, from Nihon Kagaku Sangyo Co., Ltd.) (1 part), the (meth) acrylic resin of Synthesis Example 1 (10 parts on a solution basis), Spherical particle J (0.24 parts), and Solvent AF-6 (5.76 parts), and the content was stirred to obtain an ink composition for offset printing of Example 49.

Example 50

Varnish B obtained in Example of Manufacture of varnish (54 parts), alkali blue toner (EB-18L, from Morimura Chemicals, Ltd.) (5 parts), and a carbon black (MA11, from Mitsubishi Chemical Corporation) (20 parts) were mixed, and the mixture was successively milled using a bead mill and a three-roll mill, to obtain an ink base. The ink base was added with a polyethylene wax (MC-850, from Morimura Chemicals, Ltd.) (5 parts), a metal dryer (N dryer, from Nihon Kagaku Sangyo Co., Ltd.) (1 part), the (meth)acrylic resin of Synthesis Example 1 (10 parts on a solution basis), spherical particle J (0.24 parts), and Solvent AF-6 (4.76 parts), and the content was stirred to obtain an ink composition for offset printing of Example 50.

Example 51

To 75 parts of Varnish C obtained in Example of Manufacture of varnish, added were a polyethylene wax (MC-850, from Morimura Chemicals, Ltd.) (8 parts), a metal dryer (N dryer, from Nihon Kagaku Sangyo Co., Ltd.) (1 part), the (meth)acrylic resin of Synthesis Example 1 (10 parts on a solution basis), spherical particle C (0.3 parts), and Solvent AF-6 (5.7 parts), and the content was stirred to obtain an ink composition for offset printing of Example 51.

Comparative Example 11

Varnish A obtained in Example of Manufacture of varnish (76 parts) and Disazo Yellow (Yellow 2606, from. Dainichiseika Color & Chemicals Mfg. Co., Ltd.) (12 parts) were mixed, and the mixture was successively milled using a bead, mill and a three-roll mill, to obtain an ink base. The ink base was added with a polyethylene wax (MC-850, from Morimura Chemicals, Ltd.) (5 parts), metal dryer (N dryer, from Ninon Kagaku Sangyo Co., Ltd.) (1 part), Solvent AF-6 (6 parts), and the content was stirred, to obtain an ink composition for offset printing of Comparative Example 11.

Comparative Example 12

Varnish A obtained in Example of Manufacture of varnish (70 parts) and Carmine 6B (6BC-474-2, from Sumika Color Co., Ltd.) (18 parts) were mixed, and the mixture was successively milled, using a bead mill and a three-roll mill, to obtain, an ink base. The ink base was added with a polyethylene wax (MC-850, from. Morimura Chemicals, Ltd.) (5 parts), a metal dryer (N dryer, from Ninon Kagaku Sangyo Co., Ltd.) (1 part), and Solvent AF-6 (6 parts), and the content was stirred to obtain an ink composition for offset printing of Comparative Example 12.

Comparative Example 13

Varnish A obtained in Example of Manufacture of varnish (70 parts) and phthalocyanine blue (A-721-EP, from Dainichiseika Color & Chemicals Mfg. Co., Ltd.) (18 parts) were mixed, and the mixture was successively milled using a bead mill and a three-roll mill, to obtain an ink base. The ink base was added with a polyethylene wax (MC-850, from Morimura Chemicals, Ltd.) (5 parts), a metal dryer (N dryer, from Nihon Kagaku Sangyo Co., Ltd.) (1 part), and Solvent AF-6 (6 parts), and the content was stirred to obtain an ink composition for offset printing of Comparative Example 13.

Comparative Example 14

Varnish B obtained in Example of Manufacture of varnish (64 parts), alkali blue toner (EB-18L, from Morimura Chemicals, Ltd.) (5 parts), and a carbon black (MA11, from Mitsubishi Chemical Corporation) (20 parts) were mixed, and the mixture was successively milled using a bead mill and a three-roll mill, to obtain an ink base. The ink base was added with a polyethylene wax (MC-850, from Morimura Chemicals, Ltd.) (5 parts), a metal dryer (N dryer, from Nihon Kagaku Sangyo Co., Ltd.) (1 part), and Solvent AF-6 (5 parts), and the content was stirred to obtain an ink composition for offset printing of Comparative Example 14.

Comparative Example 15

Varnish A obtained in Example of Manufacture of varnish (76 parts) and Disazo Yellow (Yellow 2606, from Dainichiseika Color & Chemicals Mfg. Co., Ltd.) (12 parts) were mixed, and the mixture was successively milled using a bead mill and a three-roll mill, to obtain an ink base. The ink base was added with a polyethylene wax (MC-850, from Morimura Chemicals, Ltd.) (5 parts), a metal dryer (N dryer, from Nihon Kagaku Sangyo Co., Ltd.) (1 part), a non-spherical particle (0.3 parts), Solvent AF-6 (5.7 parts), and the content was stirred to obtain an ink composition for offset printing of Comparative Example 15.

Comparative Example 16

Varnish A obtained in Example of Manufacture of varnish (70 parts) and Carmine 6B (6BC-474-2, from Sumika Color Co., Ltd.) (18 parts) were mixed, and the mixture was successively milled using a bead mill and a three-roll mill, to obtain an ink base. The ink base was added with a polyethylene wax (MC-850, from Morimura Chemicals, Ltd.) (5 parts), a metal dryer (N dryer, from Ninon Kagaku Sangyo Co., Ltd.) (1 part), a non-spherical particle (0.3 parts), and Solvent AF-6 (5.7 parts), and the content was stirred to obtain an ink composition for offset printing of Comparative Example 16.

Comparative Example 17

Varnish A obtained in Example of Manufacture of varnish (70 parts) and phthalocyanine blue (A-721-EP, from Dainichiseika Color & Chemicals Mfg. Co., Ltd.) (18 parts) were mixed, and the mixture was successively milled using a bead mill and a three-roll mill, to obtain an ink base. The ink base was added with a polyethylene wax (MC-850, from Morimura Chemicals, Ltd.) (5 parts), a metal dryer (N dryer, from Nihon Kagaku Sangyo Co., Ltd.) (1 part), a non-spherical particle (0.3 parts), and Solvent AF-6 (5.7 parts), and the content was stirred to obtain an ink composition for offset printing of Comparative Example 17.

Comparative Example 18

Varnish B obtained in Example of Manufacture of varnish (64 parts), alkali blue toner (EB-18L, from Morimura Chemicals, Ltd.) (5 parts), and a carbon black (MA11, from Mitsubishi Chemical Corporation) (20 parts) were mixed, and the mixture was successively milled using a bead mill and a three-roll mill, to obtain an ink base. The ink base was added with a polyethylene wax (MC-850, from Morimura Chemicals, Ltd.) (5 parts), a metal dryer (N dryer, from Nihon Kagaku Sangyo Co., Ltd.) (1 part), a non-spherical particle (0.3 parts), and Solvent AF-6 (4.7 parts), and the content was stirred to obtain an ink composition for offset printing of Comparative Example 18.

Comparative Example 19

Varnish A obtained in Example of Manufacture of varnish (76 parts) and Disazo Yellow (Yellow 2606, from. Dainichiseika Color & Chemicals Mfg. Co., Ltd.) (12 parts) were mixed, and the mixture was successively milled using a bead mill and a three-roll mill, to obtain an ink base. The ink base was added with a polyethylene wax (MC-850, from Morimura Chemicals, Ltd.) (5 parts), a metal dryer (N dryer, from Nihon Kagaku Sangyo Co., Ltd.) (1 part), Spherical particle D (0.3 parts), and Solvent AF-6 (5.7 parts), and the content was stirred to obtain an ink composition for offset printing of Comparative Example 19.

Comparative Example 20

Varnish A obtained in Example of Manufacture of varnish. (70 parts) and Carmine 6B (6BC-474-2, from Sumika Color Co., Ltd.) (18 parts) were mixed, and the mixture was successively milled using a bead mill and a three-roll mill, to obtain an ink base. The ink base was added with a polyethylene wax (MC-850, from Morimura Chemicals, Ltd.) (5 parts), a metal dryer (N dryer, from Nihon Kagaku Sangyo Co., Ltd.) (1 part), Spherical particle D (0.3 parts), and Solvent AF-6 (5.7 parts), and the content was stirred to obtain an ink composition for offset printing of Comparative Example 20.

Comparative Example 21

Varnish A obtained in Example of Manufacture of varnish (70 parts) and phthalocyanine blue (A-721-EP, from Dainichiseika Color & Chemicals Mfg. Co., Ltd.) (18 parts) were mixed, and the mixture was successively milled using a bead mill and a three-roll mill, to obtain an ink base. The ink base was added with a polyethylene wax (MC-850, from Morimura Chemicals, Ltd.) (5 parts), a metal dryer (N dryer, from Nihon Kagaku Sangyo Co., Ltd.) (1 part), Spherical particle D (0.3 parts), and Solvent AF-6 (5.7 parts), and the content was stirred to obtain an ink composition for offset printing of Comparative Example 21.

Comparative Example 22

Varnish B obtained in Example of Manufacture of varnish (64 parts), alkali blue toner (EB-18L, from Morimura Chemicals, Ltd.) (5 parts), and carbon black (MA11, from Mitsubishi Chemical Corporation) (20 parts) were mixed, and the mixture was successively milled using a bead mill and a three-roll mill, to obtain an ink base. The ink base was added with a polyethylene wax (MC-850, from Morimura Chemicals, Ltd.) (5 parts), a metal dryer (N dryer, from Nihon Kagaku Sangyo Co., Ltd.) (1 part), Spherical particle D (0.3 parts), and Solvent AF-6 (4.7 parts), and the content was stirred to obtain an ink composition for offset printing of Comparative Example 22.

Comparative Example 23

Varnish A obtained, in Example of Manufacture of varnish (70 parts) and phthalocyanine blue (A-721-EP, from Dainichiseika Color & Chemicals Mfg. Co., Ltd.) (18 parts) were mixed, and the mixture was successively milled using a bead mill and a three-roll mill, to obtain an ink base. The ink base was added with a polyethylene wax (MC-850, from Morimura Chemicals, Ltd.) (5 parts), a metal dryer (N dryer, from. Nihon Kagaku Sangyo Co., Ltd.) (1 part), Spherical particle I (0.3 parts), and Solvent AF-6 (5.7 parts), and the content was stirred to obtain an ink composition for offset printing of Comparative Example 23.

Comparative Example 24

An ink composition for offset printing was manufactured as described below, using a particle equivalent to Powder C described at paragraph [0024] in JP-A-2006-206667.

Varnish A obtained in Example of Manufacture of varnish (76 parts) and Disazo Yellow (Yellow 2606, from Dainichiseika Color & Chemicals Mfg. Co., Ltd.) (12 parts) were mixed, and the mixture was successively milled using a bead mill and a three-roll mill, to obtain an ink base. The ink base was added with a polyethylene wax (MC-850, from Morimura Chemicals, Ltd.) (5 parts), a metal dryer (N dryer, from Nihon Kagaku Sangyo Co., Ltd.) (1 part), Spherical particle K (0.24 parts), and Solvent AF-6 (5.76 parts), and the content was stirred to obtain an ink composition for offset printing of Comparative Example 24.

Comparative Example 25

An ink composition for offset printing was manufactured as described below, using a particle equivalent to Powder C described in paragraph [0024] in JP-A-2006-206667.

Varnish A obtained in Example of Manufacture of varnish (70 parts) and Carmine 6B (6BC-474-2, from Sumika Color Co., Ltd.) (18 parts) were mixed, and the mixture was successively milled using a bead mill and a three-roll mill, to obtain an ink base. The ink base was added with a polyethylene wax (MC-850, from Morimura Chemicals, Ltd.) (5 parts), a metal dryer (N dryer, from Nihon Kagaku Sangyo Co., Ltd.) (1 part), Spherical particle K (0.24 parts), and Solvent AF-6 (5.76 parts), and the content was stirred to obtain an ink composition for offset printing of Comparative Example 25.

Comparative Example 26

An ink composition for offset printing was manufactured as described below, using a particle equivalent to Powder C described in paragraph [0024] in JP-A-2006-206667.

Varnish A obtained in Example of Manufacture of varnish (70 parts) and phthalocyanine blue (A-721-EP, from Dainichiseika Color & Chemicals Mfg. Co., Ltd.) (18 parts) were mixed, and the mixture was successively milled using a bead mill and a three-roll mill, to obtain an ink base. The ink base was added with a polyethylene wax (MC-850, from Morimura Chemicals, Ltd.) (5 parts), a metal dryer (N dryer, from. Nihon Kagaku Sangyo Co., Ltd.) (1 part), Spherical particle K (0.24 parts), and Solvent AF-6 (5.76 parts), and the content was stirred to obtain an ink composition for offset printing of Comparative Example 26.

Comparative Example 27

An ink composition for offset printing was manufactured as described below, using a particle equivalent to Powder C described in paragraph [0024] in JP-A-2006-206667.

Varnish B obtained, in Example of Manufacture of varnish (64 parts), alkali blue toner (EB-18L, from Morimura Chemicals, Ltd.) (5 parts), and a carbon black (MA11, from Mitsubishi Chemical Corporation) (20 parts) were mixed, and the mixture was successively milled using a bead mill and a three-roll mill, to obtain an ink base. The ink base was added with a polyethylene wax (MC-850, from Morimura Chemicals, Ltd.) (5 parts), a metal dryer (N dryer, from Nihon Kagaku Sangyo Co., Ltd.) (1 part), Spherical particle K (0.24 parts), and Solvent AF-6 (4.76 parts), and the content was stirred to obtain an ink composition for offset printing of Comparative Example 27.

Comparative Example 28

Varnish C obtained, in Example of Manufacture of varnish (82 parts), a polyethylene wax (MC-850, from Morimura Chemicals, Ltd.) (8 parts), a metal dryer (N dryer, from Nihon Kagaku Sangyo Co., Ltd.) (1 part), and Solvent AF-6 (9 parts) were mixed, and the content was stirred to obtain an ink composition for offset printing of Comparative Example 28.

Performance Evaluation Test of Acrylic Resin-Containing Ink Composition for Offset Printing Printing performances of the ink compositions for offset printing of Examples 1 to 20 and 29, and Comparative Examples 1 to 7 and 13 were examined by the evaluation tests below, and results were summarized in Tables 4 and 5.

Set-Dryability Test

Test specimens were prepared by applying the sheetfed offset inks of Examples 1 to 20 and 29 and Comparative Examples 1 to 7 and 13, using an RI tester from Mei Seisakusho Co., Ltd., at an ink feed of 0.075 ml over four-section rubber rolls, respectively onto "OK Top Coat Plus" from Oil Paper Co., Ltd. as a representative of fast, setting paper, and onto "Mitsubishi Art." from Mitsubishi Paper Mills Ltd, as a representative of slow setting paper. Immediately after applying the inks, degrees of adhesion of ink onto a woodfree paper were observed using an automated ink setting-drying tester from Hoei-Seiko Printing Co., Ltd., to measure how long (minutes) does it take that the ink became non-adhesive. The shorter the time, the better the setting. The test was carried out at normal temperature without heating.

Resin Dispersibility

Dispersibility of resin in the process of adding the acrylic resin to the ink compositions for offset printing in Examples 1 to 14 and 29 and Comparative Examples 1 to 3 and 13 were evaluated as follows:

○ . . . being liquid or viscous matter at normal temperature (25° C.);

Δ . . . being solid or likely to solidify at or below normal temperature (25° C.), allowing the acrylic resin to easily mix into the solvent when liquefied under heating; and x . . . being solid or likely to solidify at or below normal temperature (25° C.), making the acrylic resin and the solvent separate and difficult to mix when liquefied under heating, Compatibility Compatibility between the acrylic resin and the ink compositions, after the acrylic resin was added to the ink compositions for offset printing in Examples 1 to 14 and 29 and Comparative Examples 1 to 3 and 13, was evaluated as follows:

○ . . . easily dispersible when added to the ink composition;

Δ . . . A when added to the ink composition, the acrylic resin was dispersible, but with slight incompatibility; and x . . . when added to the ink composition, the resin was not dispersible but coagulated therein.

Performance Evaluation Test of Resin

The ink compositions for offset printing in Examples 1, 2, 8 and 15 to 20 and Comparative Examples 1, 2, 4 to 7 and 13, which are varied in the amount of addition of (meth) acrylic resin, were subjected to set-dryability test. Results of the test were summarized in Table 5. The measurement was conducted in the same way as described above, using OK Top Coat Plus and Mitsubishi Art as the test papers. The test was conducted at room temperature without heating.

The fewer the amount of addition capable of accelerating the set-dryability, the better. Meanwhile, if the set-dryability remained unchanged or almost unchanged despite the amount of addition of the resin was increased, the resin is poor in the set-dryability.

TABLE 4

| Ink composition | | Example 1 | Example 2 | Example 3 | Example 4 | Example 5 | Example 6 |
|---|---|---|---|---|---|---|---|
| Colorant | Phthalocyanine blue | 18 | 18 | 18 | 18 | 18 | 18 |
| Varnish | Varnish A | 60 | 60 | 60 | 60 | 60 | 60 |
| | Varnish B | | | | | | |
| Wax | Polyethylene wax | 5 | 5 | 5 | 5 | 5 | 5 |
| Dryer | N dryer | 1 | 1 | 1 | 1 | 1 | 1 |
| Petroleum solvent | Solvent AF-6 | 6 | 6 | 6 | 6 | 6 | 6 |
| (Meth)acrylic resin | Type | Synthesis Example 1 | Synthesis Example 2 | Synthesis Example 3 | Synthesis Example 4 | Synthesis Example 5 | Synthesis Example 6 |
| | Amount of mixing | 10 | 10 | 10 | 10 | 10 | 10 |
| Particle | Type | — | — | — | — | — | — |
| | Amount of mixing | — | — | — | — | — | — |
| Setting | OK Top Coat | 2 | 2 | 2 | 2 | 2 | 2.5 |
| | Mitsubishi Art | 11 | 10 | 10 | 9 | 11 | 11 |
| Dispersibility of resin | | ○ | ○ | ○ | ○ | ○ | ○ |
| Compatibility | | ○ | ○ | ○ | ○ | ○ | ○ |

| Ink composition | | Example 7 | Example 8 | Example 9 | Example 10 | Example 11 |
|---|---|---|---|---|---|---|
| Colorant | Phthalocyanine blue | 18 | 18 | 18 | 18 | 18 |
| Varnish | Varnish A | 60 | 60 | 60 | 60 | 60 |
| | Varnish B | | | | | |
| Wax | Polyethylene wax | 5 | 5 | 5 | 5 | 5 |
| Dryer | N dryer | 1 | 1 | 1 | 1 | 1 |
| Petroleum solvent | Solvent AF-6 | 6 | 6 | 6 | 6 | 6 |

TABLE 4-continued

| (Meth)acrylic resin | Type | Synthesis Example 7 | Synthesis Example 8 | Synthesis Example 9 | Synthesis Example 10 | Synthesis Example 11 |
|---|---|---|---|---|---|---|
| | Amount of mixing | 10 | 10 | 10 | 10 | 10 |
| Particle | Type | — | — | — | — | — |
| | Amount of mixing | — | — | — | — | — |
| Setting | OK Top Coat | 2.5 | 3 | 2.5 | 1.5 | 2.5 |
| | Mitsubishi Art | 12 | 12 | 11 | 10 | 10 |
| Dispersibility of resin | | ○ | ○ | ○ | Δ | Δ |
| Compatibility | | ○ | ○ | ○ | ○ | ○ |

| Ink composition | | Example 12 | Example 13 | Example 14 | Example 29 | Comparative Example 1 |
|---|---|---|---|---|---|---|
| Colorant | Phthalocyanine blue | 18 | 18 | 18 | 18 | 18 |
| Varnish | Varnish A | 60 | 60 | 60 | 60 | 60 |
| | Varnish B | | | | | |
| Wax | Polyethylene wax | 5 | 5 | 5 | 5 | 5 |
| Dryer | N dryer | 1 | 1 | 1 | 1 | 1 |
| Petroleum solvent | Solvent AF-6 | 6 | 6 | 6 | 5.7 | 6 |
| (Meth)acrylic resin | Type | Synthesis Example 12 | Synthesis Example 13 | Synthesis Example 14 | Synthesis Example 1 | Comparative Synthesis A |
| | Amount of mixing | 10 | 10 | 10 | 10 | 10 |
| Particle | Type | — | — | — | Spherical particle C | — |
| | Amount of mixing | — | — | — | 0.3 | — |
| Setting | OK Top Coat | 2.5 | 2 | 2 | 2.5 | 3.5 |
| | Mitsubishi Art | 12 | 10 | 8 | 11 | 17 |
| Dispersibility of resin | | ○ | Δ | Δ | ○ | ○ |
| Compatibility | | ○ | ○ | Δ | ○ | ○ |

| Ink composition | | Comparative Example 2 | Comparative Example 3 | Comparative Example 13 |
|---|---|---|---|---|
| Colorant | Phthalocyanine blue | 18 | 18 | 18 |
| Varnish | Varnish A | 60 | 60 | 70 |
| | Varnish B | | | |
| Wax | Polyethylene wax | 5 | 5 | 5 |
| Dryer | N dryer | 1 | 1 | 1 |
| Petroleum solvent | Solvent AF-6 | 6 | 6 | 6 |
| (Meth)acrylic resin | Type | Comparative Synthesis B | Comparative Synthesis D | — |
| | Amount of mixing | 10 | 10 | — |
| Particle | Type | — | — | — |
| | Amount of mixing | — | — | — |
| Setting | OK Top Coat | 3.5 | 2 | 4 |
| | Mitsubishi Art | 16 | 8 | 17 |
| Dispersibility of resin | | X | Δ | — |
| Compatibility | | ○ | X | — |

In Table 4, the values of the amount of mixing are given in "part (s) by weight".

TABLE 5

| Ink composition | | Example 15 | Example 1 | Example 16 | Example 17 | Example 2 |
|---|---|---|---|---|---|---|
| Colorant | Phthalocyanine blue | 18 | 18 | 18 | 18 | 18 |
| Varnish | Varnish A | 65 | 60 | 55 | 65 | 60 |
| | Varnish B | | | | | |
| Wax | Polyethylene wax | 5 | 5 | 5 | 5 | 5 |
| Dryer | N Dryer | 1 | 1 | 1 | 1 | 1 |
| Petroleum solvent | Solvent AF-6 | 6 | 6 | 6 | 6 | 6 |
| (Meth)acrylic resin | Type | Synthesis Example 1 | Synthesis Example 1 | Synthesis Example 1 | Synthesis Example 2 | Synthesis Example 2 |
| | Amount of mixing | 5 | 10 | 15 | 5 | 10 |
| Setting performance | OK Top Coat | 2.5 | 2 | 1.5 | 2.5 | 2 |
| | Mitsubishi Art | 12 | 11 | 10 | 12 | 10 |

TABLE 5-continued

| Ink composition | | Example 18 | Example 19 | Example 8 | Example 20 |
|---|---|---|---|---|---|
| Colorant | Phthalocyanine blue | 18 | 18 | 18 | 18 |
| Varnish | Varnish A | 55 | 65 | 60 | 55 |
| | Varnish B | | | | |
| Wax | Polyethylene wax | 5 | 5 | 5 | 5 |
| Dryer | N Dryer | 1 | 1 | 1 | 1 |
| Petroleum solvent | Solvent AF-6 | 6 | 6 | 6 | 6 |
| (Meth)acrylic resin | Type | Synthesis Example 2 | Synthesis Example 8 | Synthesis Example 8 | Synthesis Example 8 |
| | Amount of mixing | 15 | 5 | 10 | 15 |
| Setting performance | OK Top Coat | 1 | 3 | 3 | 2.5 |
| | Mitsubishi Art | 8 | 14 | 12 | 11 |

| Ink composition | | Comparative Example 4 | Comparative Example 1 | Comparative Example 5 | Comparative Example 6 | Comparative Example 2 | Comparative Example 7 | Comparative Example 13 |
|---|---|---|---|---|---|---|---|---|
| Colorant | Phthalocyanine blue | 18 | 18 | 18 | 18 | 18 | 18 | 18 |
| Varnish | Varnish A | 65 | 60 | 55 | 65 | 60 | 55 | 70 |
| | Varnish B | | | | | | | |
| Wax | Polyethylene wax | 5 | 5 | 5 | 5 | 5 | 5 | 5 |
| Dryer | N Dryer | 1 | 1 | 1 | 1 | 1 | 1 | 1 |
| Petroleum solvent | Solvent AF-6 | 6 | 6 | 6 | 6 | 6 | 6 | 6 |
| (Meth)acrylic resin | Type | Comparative Synthesis A | Comparative Synthesis A | Comparative Synthesis A | Comparative Synthesis B | Comparative Synthesis B | Comparative Synthesis B | — |
| | Amount of mixing | 5 | 10 | 15 | 5 | 10 | 15 | — |
| Setting performance | OK Top Coat | 4 | 3.5 | 3.5 | 4 | 3.5 | 3.5 | 4 |
| | Mitsubishi Art | 17 | 17 | 17 | 17 | 16 | 15 | 17 |

In Table 5, the values of the amount of mixing are given in "part(s) by weight".

Performance Evaluation Test of Spherical Particle-Containing Ink Composition for Offset Printing (1)

Printing performance of the ink compositions for offset printing of Examples 21, 22 and 29 and Comparative Examples 13, 17 and 23 were evaluated as described below. Results were summarized in Table 6.

Slippage Test

Test specimens were prepared by applying the ink compositions for offset printing of Examples 21, 22 and 29 and Comparative Examples 13, 17 and 23, using an RI tester from Mel Seisakusho Co., Ltd., at an ink feed of 0.2 ml over two-section rubber rolls, on an art paper. Then slippage between the tinted face of each test specimen and the blank face of the coated paper was measured using HEIDON-10 from Shinto Scientific Co., Ltd. under a load of 60 g, and evaluated according to the criteria below. The larger the slippage, the easier the inspection during printing. The ink composition is practically acceptable if ranked at Δ or above.

Evaluation criteria:
○ good slippage;
Δ . . . fair slippage; and
x . . . no slippage due to strong sticking.

Offset Test

Test specimens were prepared by applying the ink compositions for offset printing of Examples 21, 22 and 29 and Comparative Examples 13, 17 and 23, using an RI tester from Mei Seisakusho Co., Ltd., at an ink feed of 0.15 ml over four-section rubber rolls, on an art paper. Then the tinted face of each test specimen and the blank face of coated paper were opposed and stacked, the degree of ink transfer onto the blank paper was observed using an ink dryability tester from Toyo Seiki Seisaku-Sho, Ltd., and evaluated according to the criteria below. Those causing less adhesion of ink onto the blank face are less likely to cause offset. The test was conducted at normal temperature without heating.

Evaluation Criteria:
○ . . . almost no dirt found on blank face;
Δ . . . slight dirt on blank face;
x . . . dirt found, on blank face; and
xx . . . tinted face and blank face adhered,

TABLE 6

| Ink Composition | | Example 21 | Example 22 | Example 29 | Comparative Example 13 | Comparative Example 17 | Comparative Example 23 |
|---|---|---|---|---|---|---|---|
| Colorant | Phthalocyanine blue | 18 | 18 | 18 | 18 | 18 | 18 |
| Varnish | Varnish A | 70 | 70 | 60 | 70 | 70 | 70 |
| | Varnish B | | | | | | |
| Wax | Polyethylene wax | 5 | 5 | 5 | 5 | 5 | 5 |

TABLE 6-continued

| Ink Composition | | Example 21 | Example 22 | Example 29 | Comparative Example 13 | Comparative Example 17 | Comparative Example 23 |
|---|---|---|---|---|---|---|---|
| Dryer | N dryer | 1 | 1 | 1 | 1 | 1 | 1 |
| Petroleum solvent | Solvent AF-6 | 5.7 | 5.7 | 5.7 | 6 | 5.7 | 5.7 |
| (Meth)acrylic resin | Type | — | — | Synthesis Example 1 | — | — | — |
| | Amount of addition | — | — | 10 | — | — | — |
| Particle | Type | Spherical particle A | Spherical particle B | Spherical particle C | — | Non-spherical particle | Spherical particle I |
| | Amount of addition | 0.3 | 0.3 | 0.3 | — | 0.3 | 0.3 |
| Slippage | | ○ | ○ | ○ | X | Δ | X |
| Offset | | ○ | ○ | ○ | XX | X | X |

In Table 6, the values of the amount of mixing are given in "part(s) by weight".

Performance Evaluation Tests of Spherical Particle-Containing Ink Composition for Offset Printing (2)

Printing performances of the ink compositions for offset printing of Examples 23 to 26 and Comparative Examples 8, 9 and 13 were examined by the evaluation tests below, Results were summarized in Table 7.

Glossiness

The ink compositions for offset printing of Examples 23 to 26 and Comparative Examples 8, 9 and 13 were transferred to the papers, using an RI tester from Mei Seisakusho Co., Ltd., at an ink feed of 0.100 ml over two-section rubber rolls. Results of measurement were summarized in Table 7, Glossiness was measured 24 hours after the transfer, using a handy glossimeter "Gloss Checker IG-330" from Horiba, Ltd.

Transferability

The ink compositions for offset printing of Examples 23 to 26 and Comparative Examples 8, 9 and 13 were transferred to the papers, using an RI tester from Mei Seisakusho Co., Ltd., at an ink feed of 0.100 ml over two-section rubber rolls, and the transferability was visually observed 24 hours after. Results of evaluation of transferability, according to the evaluation criteria below, were summarized in Table 7.

Evaluation Criteria:
○ . . . good transferability;
Δ . . . slightly poor transferability; and
x . . . transfer failure observed.

In Table 7, the values of the amount of mixing are given in "part(s) by weight".

Now it has been known that addition of an auxiliary agent such as wax component, anti-offset agent or the like degrades the glossiness of the obtainable printed matter. However, as is clear from comparison between Examples 23 to 26 and Comparative Example 13, the ink composition of Examples 23 to 26 succeeded, despite addition of the spherical particle, in keeping the gloss equivalent to that attainable by the ink composition of Comparative Example 13 having no spherical particle contained therein.

Performance Evaluation Test of Ink Composition for Offset Printing Containing Acrylic Resin and Particle Printing performances of the ink compositions for offset printing of Example 27 to 51 and Comparative Examples 11 to 28 were examined by the evaluation tests below. Results were summarized in Tables 8 to 10. The tests were conducted at normal temperature without heating.

Printing Condition: Wet Printing
Printing press: Speed Master, from Heidelberg Druckmaschinen AG
Printing papers:
  Coated paper: OK Top Coat Plus, from Oji Paper Co., Ltd.
  Art paper: Tokubishi Art double-side, from Mitsubishi Paper Mills, Ltd.
  Matte paper: U-LITE, from. Nippon Paper Industries, Ltd.
Printing plate: XP-F, from Fujifilm Corporation
Printing speed: 10,000 sheets/h

TABLE 7

| Ink composition | | Example 23 | Example 24 | Comparative Example 8 | Example 25 | Example 26 | Comparative Example 9 | Comparative Example 13 |
|---|---|---|---|---|---|---|---|---|
| Colorant | Phthalocyanine blue | 18 | 18 | 18 | 18 | 18 | 18 | 18 |
| Varnish | Varnish A Varnish B | 69.5 | 69 | 65 | 69.5 | 69 | 65 | 70 |
| Wax | Polyethylene wax | 5 | 5 | 5 | 5 | 5 | 5 | 5 |
| Dryer | N dryer | 1 | 1 | 1 | 1 | 1 | 1 | 1 |
| Petroleum solvent | Solvent AF-6 | 6 | 6 | 6 | 6 | 6 | 6 | 6 |
| Particle | Type | Spherical particle A | Spherical particle A | Spherical particle A | Spherical particle B | Spherical particle B | Spherical particle B | — |
| | Amount of mixing | 0.5 | 1 | 5 | 0.5 | 1 | 5 | — |
| Coated paper | Glossiness | 68 | 63 | 47 | 66 | 63 | 46 | 68 |
| | Transferabiity | ○ | ○ | Δ | ○ | Δ | X | ○ |
| Art paper | Glossiness | 85 | 82 | 75 | 84 | 82 | 73 | 85 |
| | Transferability | ○ | ○ | Δ | ○ | Δ | X | ○ |

Offset Resistance in Multicolor Printing

A designed pattern composed of a four-color overlaid area, a three-color overlaid area, a two-color overlaid area and a single-color area was printed on 5000 sheets, the sheets were vertically stacked, and offset on the lowermost printed matter was evaluated 24 hours after, according to the criteria below. The ink composition is judged to be effective in reducing the amount of consumption of a spray powder, if ranked at Δ or above.

Evaluation Criteria:
⊚ . . . no dirt found on back, even without spray powder;
○ . . . slight dirt found on back, but cleared by using spray powder-reduced to one-fourth the conventional amount;
Δ . . . slight dirt found on back, but cleared by using spray powder reduced to half the conventional amount;
x . . . dirt found on back, even with an equivalent amount of spray powder as before; and
xx . . . back face and printed face adhered to form a block, failed in reducing spray powder.

Piling Performance

In a comparative study of piling-up on rollers, 5000 sheets were printed using the aforementioned printing press, and the degree of piling-up on the blanket and rollers was checked visually and by finger touch, and evaluated according to the criteria below. Evaluation criteria:
○ . . . no piling-up;
Δ . . . slight piling-up; and
x . . . piled up.

Time Interval before Printing on Opposite Face

The sheets were printed on one faces using a printing press, and then printed on the back faces one hour after, 3 hours after, hours after, and 7 hours after, respectively, and evaluated as follows. Results were summarized in Table 10. The shorter the time interval before printing on the opposite face, the higher the productivity.

Evaluation Criteria:
○ . . . no scratch found on the previously printed face, after printing on the opposite face;
Δ . . . scratch found on the previously printed face, although printing was allowed on the opposite face; and
x printing not possible due to incomplete drying.

Time Interval before Cutting

The sheets were printed on one faces, and cut one hour after, 3 hours after, and 6 hours after, respectively. Whether the ink adhered to the back faces or not was evaluated as follows, and results were summarized in Table 10. The shorter the time interval before the ink becomes non-adhesive, the higher the productivity,
○ . . . no adhesion;
Δ . . . slight adhesion; and
x . . . adhesion.

Printing performances of the ink compositions for offset printing of Examples 27 to 30 and Comparative Examples 11 to 14 were examined by the evaluation tests below. Results were summarized in Table 10.

Printing condition: Waterless printing
Printing press: Speed. Master, from Heidelberg Druckmaschinen AG
Printing plate: VG5, from Toray Industries, Inc.
Printing papers below were used.
Printing papers:
Coated, paper: OK Top Coat Plus, from Oji Paper Co., Ltd.
Matte paper: U-LITE, from Nippon Paper Industries, Ltd.

Scumming Resistance

Finish quality of the printed matter obtained, by waterless printing was evaluated as follows, and results were summarized in Table 10.
○ . . . high quality of printing; and
x . . . stained during printing.

TABLE 8

| Ink compoisition | | Example 27 | Example 28 | Example 29 | Example 30 | Example 31 | Example 32 |
|---|---|---|---|---|---|---|---|
| Colorant | Disazo yellow | 12 | | | | 12 | |
| | Carmine 6B | | 18 | | | | 18 |
| | Phthalocyanine blue | | | 18 | | | |
| | Alkali blue toner | | | | 5 | | |
| | Carbon black | | | | 20 | | |
| Varnish | VarnishA | 66 | 60 | 60 | | 66 | 60 |
| | VarnishB | | | | 54 | | |
| Wax | Polyethylene wax | 5 | 5 | 5 | 5 | 5 | 5 |
| Dryer | N dryer | 1 | 1 | 1 | 1 | 1 | 1 |
| Petroleum solvent | Solvent AF-6 | 5.7 | 5.7 | 5.7 | 4.7 | 5.7 | 5.7 |
| (Meth)acrylic resin | Type | Synthesis Example 1 | Synthesis Example 1 | Synthesis Example 1 | Synthesis Example 1 | Synthesis Example 1 | Synthesis Example 1 |
| | Amount of mixing | 10 | 10 | 10 | 10 | 10 | 10 |
| Particle | Type | Spherical particle C | Spherical particle C | Spherical particle C | Spherical particle C | Spherical particle E | Spherical particle E |
| | Amount of mixing | 0.3 | 0.3 | 0.3 | 0.3 | 0.3 | 0.3 |
| Offset resistance | Coated paper | | ⊚ | | | ⊚ | |
| | Art paper | | ⊚ | | | ⊚ | |
| | Matte paper | | ⊚ | | | ⊚ | |
| Piling performance | | | ○ | | | ○ | |

| Ink compoisition | | Example 33 | Example 34 | Example 35 | Example 36 | Example 37 | Example 38 |
|---|---|---|---|---|---|---|---|
| Colorant | Disazo yellow | | | 12 | | | |
| | Carmine 6B | | | | 18 | | |
| | Phthalocyanine blue | 18 | | | | 18 | |
| | Alkali blue toner | | 5 | | | | 5 |
| | Carbon black | | 20 | | | | 20 |

TABLE 8-continued

| | | | | | | | |
|---|---|---|---|---|---|---|---|
| Varnish | VarnishA | 60 | | 66 | 60 | 60 | |
| | VarnishB | | 54 | | | | 54 |
| Wax | Polyethylene wax | 5 | 5 | 5 | 5 | 5 | 5 |
| Dryer | N dryer | 1 | 1 | 1 | 1 | 1 | 1 |
| Petroleum solvent | Solvent AF-6 | 5.7 | 4.7 | 5.7 | 5.7 | 5.7 | 4.7 |
| (Meth)acrylic resin | Type | Synthesis Example 1 | Synthesis Example 1 | Synthesis Example 1 | Synthesis Example 1 | Synthesis Example 1 | Synthesis Example 1 |
| | Amount of mixing | 10 | 10 | 10 | 10 | 10 | 10 |
| Particle | Type | Spherical particle E | Spherical particle E | Spherical particle F | Spherical particle F | Spherical particle F | Spherical particle F |
| | Amount of mixing | 0.3 | 0.3 | 0.3 | 0.3 | 0.3 | 0.3 |
| Offset resistance | Coated paper | ◎ | | | | ◎ | |
| | Art paper | ◎ | | | | ◎ | |
| | Matte paper | ◎ | | | | ◎ | |
| Piling performance | | ○ | | | | ○ | |

| Ink composition | | Example 39 | Example 40 | Example 41 | Example 42 | Example 43 | Example 44 |
|---|---|---|---|---|---|---|---|
| Colorant | Disazo yellow | 12 | | | | 12 | |
| | Carmine 6B | | 18 | | | | 18 |
| | Phthalocyanine blue | | | 18 | | | |
| | Alkali blue toner | | | | 5 | | |
| | Carbon black | | | | 20 | | |
| Varnish | VarnishA | 66 | 60 | 60 | | 66 | 60 |
| | VarnishB | | | | 54 | | |
| Wax | Polyethylene wax | 5 | 5 | 5 | 5 | 5 | 5 |
| Dryer | N dryer | 1 | 1 | 1 | 1 | 1 | 1 |
| Petroleum solvent | Solvent AF-6 | 5.7 | 5.7 | 5.7 | 4.7 | 5.7 | 5.7 |
| (Meth)acrylic resin | Type | Synthesis Example 1 | Synthesis Example 1 | Synthesis Example 1 | Synthesis Example 1 | Synthesis Example 1 | Synthesis Example 1 |
| | Amount of mixing | 10 | 10 | 10 | 10 | 10 | 10 |
| Particle | Type | Spherical particle G | Spherical particle G | Spherical particle G | Spherical particle G | Spherical particle H | Spherical particle H |
| | Amount of mixing | 0.3 | 0.3 | 0.3 | 0.3 | 0.3 | 0.3 |
| Offset resistance | Coated paper | | ◎ | | | ◎ | |
| | Art paper | | ◎ | | | ○ | |
| | Matte paper | | ◎ | | | ○ | |
| Piling performance | | | ○ | | | Δ | |

| Ink composition | | Example 45 | Example 46 | Example 47 | Example 48 | Example 49 | Example 50 |
|---|---|---|---|---|---|---|---|
| Colorant | Disazo yellow | | | 12 | | | |
| | Carmine 6B | | | | 18 | | |
| | Phthalocyanine blue | 18 | | | | 18 | |
| | Alkali blue toner | | 5 | | | | 5 |
| | Carbon black | | 20 | | | | 20 |
| Varnish | VarnishA | 60 | | 66 | 60 | 60 | |
| | VarnishB | | 54 | | | | 54 |
| Wax | Polyethylene wax | 5 | 5 | 5 | 5 | 5 | 5 |
| Dryer | N dryer | 1 | 1 | 1 | 1 | 1 | 1 |
| Petroleum solvent | Solvent AF-6 | 5.7 | 4.7 | 5.76 | 5.76 | 5.76 | 4.76 |
| (Meth)acrylic resin | Type | Synthesis Example 1 | Synthesis Example 1 | Synthesis Example 1 | Synthesis Example 1 | Synthesis Example 1 | Synthesis Example 1 |
| | Amount of mixing | 10 | 10 | 10 | 10 | 10 | 10 |
| Particle | Type | Spherical particle H | Spherical particle H | Spherical particle J | Spherical particle J | Spherical particle J | Spherical particle J |
| | Amount of mixing | 0.3 | 0.3 | 0.24 | 0.24 | 0.24 | 0.24 |
| Offset resistance | Coated paper | | ◎ | | | ◎ | |
| | Art paper | | ○ | | | Δ | |
| | Matte paper | | ○ | | | ○ | |
| Piling performance | | | Δ | | | Δ | |

| Ink composition | | Comp. Example 11 | Comp. Example 12 | Comp. Example 13 | Comp. Example 14 | Comp. Example 15 | Comp. Example 16 | Comp. Example 17 | Comp. Example 18 |
|---|---|---|---|---|---|---|---|---|---|
| Colorant | Disazo yellow | 12 | | | | 12 | | | |
| | Carmine 6B | | 18 | | | | 18 | | |
| | Phthalocyanine blue | | | 18 | | | | 18 | |
| | Alkali blue toner | | | | 5 | | | | 5 |
| | Carbon black | | | | 20 | | | | 20 |
| | Talc | | | | | | | | |

TABLE 8-continued

| Varnish | Varnish A | 76 | 70 | 70 |  | 76 | 70 | 70 |  |
|---|---|---|---|---|---|---|---|---|---|
|  | Varnish B |  |  |  | 64 |  |  |  | 64 |
|  | Varnish C |  |  |  |  |  |  |  |  |
| Wax | Polyethylene wax | 5 | 5 | 5 | 5 | 5 | 5 | 5 | 5 |
| Dryer | N dryer | 1 | 1 | 1 | 1 | 1 | 1 | 1 | 1 |
| Petroleum solvent | Solvent AF-6 | 6 | 6 | 6 | 5 | 5.7 | 5.7 | 57 | 4.7 |
| (Meth)acrylic resin | Type | — | — | — | — | — | — | — | — |
|  | Amount of mixing | — | — | — | — | — | — | — | — |
| Particle | Type | — | — | — | — | Non-spherical particle | Non-spherical particle | Non-spherical particle | Non-spherical particle |
|  | Amount of mixing | — | — | — | — | 0.3 | 0.3 | 0.3 | 0.3 |
| Offset resistance | Coated paper |  | X |  |  |  | Δ |  |  |
|  | Art paper |  | XX |  |  |  | X |  |  |
|  | Matte paper |  | X |  |  |  | X |  |  |
| Piling performance |  |  | ○ |  |  |  | Δ |  |  |

| Ink compoistion |  | Comp. Example 19 | Comp. Example 20 | Comp. Example 21 | Comp. Example 22 | Comp. Example 24 | Comp. Example 25 | Comp. Example 26 | Comp. Example 27 |
|---|---|---|---|---|---|---|---|---|---|
| Colorant | Disazo yellow | 12 |  |  |  | 12 |  |  |  |
|  | Carmine 6B |  | 18 |  |  |  | 18 |  |  |
|  | Phthalocyanine blue |  |  | 18 |  |  |  | 18 |  |
|  | Alkali blue toner |  |  |  | 5 |  |  |  | 5 |
|  | Carbon black |  |  |  | 20 |  |  |  | 20 |
|  | Talc |  |  |  |  |  |  |  |  |
| Varnish | Varnish A | 76 | 70 | 70 |  | 76 | 70 | 70 |  |
|  | Varnish B |  |  |  | 64 |  |  |  | 64 |
|  | Varnish C |  |  |  |  |  |  |  |  |
| Wax | Polyethylene wax | 5 | 5 | 5 | 5 | 5 | 5 | 5 | 5 |
| Dryer | N dryer | 1 | 1 | 1 | 1 | 1 | 1 | 1 | 1 |
| Petroleum solvent | Solvent AF-6 | 5.7 | 5.7 | 5.7 | 4.7 | 5.76 | 5.76 | 5.76 | 4.76 |
| (Meth)acrylic resin | Type | — | — | — | — | — | — | — | — |
|  | Amount of mixing | — | — | — | — | — | — | — | — |
| Particle | Type | Spherical particle D | Spherical particle D | Spherical particle D | Spherical particle D | Spherical particle K | Spherical particle K | Spherical particle K | Spherical particle K |
|  | Amount of mixing | 0.3 | 0.3 | 0.3 | 0.3 | 0.24 | 0.24 | 0.24 | 0.24 |
| Offset resistance | Coated paper |  | Δ |  |  |  | ○ |  |  |
|  | Art paper |  | Δ |  |  |  | Δ |  |  |
|  | Matte paper |  | Δ |  |  |  | Δ |  |  |
| Piling performance |  |  | X |  |  |  | X |  |  |

In Table 8, the values of the amount of mixing are given in "part(s) by weight".

TABLE 9

| Ink composition |  | Example 27 | Example 28 | Example 29 | Example 30 | Example 51 | Comparative Example 11 |
|---|---|---|---|---|---|---|---|
| Colorant | Disazo yellow | 12 |  |  |  |  | 12 |
|  | Carmine 6B |  | 18 |  |  |  |  |
|  | Phthalocyanine blue |  |  | 18 |  |  |  |
|  | Alkali blue toner |  |  |  | 5 |  |  |
|  | Carbon black |  |  |  | 20 |  |  |
| Varnish | Varnish A | 66 | 60 | 60 |  |  | 76 |
|  | Varnish B |  |  |  | 54 |  |  |
|  | Varnish C |  |  |  |  | 75 |  |
| Wax | Polyethylene wax | 5 | 5 | 5 | 5 | 8 | 5 |
| Dryer | N Dryer | 1 | 1 | 1 | 1 | 1 | 1 |
| Petroleum solvent | Solvent AF-6 | 5.7 | 5.7 | 5.7 | 4.7 | 5.7 | 6 |
| (Meth)acrylic resin | Type | Synthesis Example 1 | Synthesis Example 1 | Synthesis Example 1 | Synthesis Example 1 | Synthesis Example 1 | — |
|  | Amount of mixing | 10 | 10 | 10 | 10 | 10 | — |
| Particle | Type | Spherical particle C | Spherical particle C | Spherical particle C | Spherical particle C | Spherical particle C | — |
|  | Amount of mixing | 0.3 | 0.3 | 0.3 | 0.3 | 0.3 | — |

TABLE 9-continued

| | | | | Comparative Example 12 | Comparative Example 13 | Comparative Example 14 | Comparative Example 28 |
|---|---|---|---|---|---|---|---|
| Offset resistance | Coated paper | | ⊚ | | | X | |
| | Art paper | | ⊚ | | | XX | |
| | Matte paper | | ⊚ | | | X | |
| Piling performance | | | ○ | | | ○ | |

| Ink composition | | Comparative Example 12 | Comparative Example 13 | Comparative Example 14 | Comparative Example 28 |
|---|---|---|---|---|---|
| Colorant | Disazo yellow | | | | |
| | Carmine 6B | 18 | | | |
| | Phthalocyanine blue | | 18 | | |
| | Alkali blue toner | | | 5 | |
| | Carbon black | | | 20 | |
| Varnish | Varnish A | 70 | 70 | | |
| | Varnish B | | | 64 | |
| | Varnish C | | | | 82 |
| Wax | Polyethylene wax | 5 | 5 | 5 | 8 |
| Dryer | N Dryer | 1 | 1 | 1 | 1 |
| Petroleum solvent | Solvent AF-6 | 6 | 6 | 5 | 9 |
| (Meth)acrylic resin | Type | — | — | — | — |
| | Amont of mixing | — | — | — | — |
| Particle | Type | — | — | — | — |
| | Amount of mixing | — | — | — | — |
| Offset resistance | Coated paper | | | X | |
| | Art paper | | | XX | |
| | Matte paper | | | X | |
| Piling performance | | | | ○ | |

In Table 9, the values of the amount of mixing are given in "part(s) by weight".

TABLE 10

| Ink composition | | Example 27 | Example 28 | Example 29 | Example 30 | Comparative Example 11 | Comparative Example 12 | Comparative Example 13 | Comparative Example 14 |
|---|---|---|---|---|---|---|---|---|---|
| Colarant | Disazo yellow | 12 | | | | 12 | | | |
| | Carmine 6B | | 18 | | | | 18 | | |
| | Phthalocyanine blue | | | 18 | | | | 18 | |
| | Alkali blue toner | | | | 5 | | | | 5 |
| | Carbon black | | | | 20 | | | | 20 |
| Varnish | Varnish A | 66 | 60 | 60 | | 76 | 70 | 70 | |
| | Varnish B | | | | 54 | | | | 64 |
| Wax | Polyethylene wax | 5 | 5 | 5 | 5 | 5 | 5 | 5 | 5 |
| Dryer | N Dryer | 1 | 1 | 1 | 1 | 1 | 1 | 1 | 1 |
| Petroleum solvent | Solvent AF-6 | 5.7 | 5.7 | 5.7 | 4.7 | 6 | 6 | 6 | 5 |
| (Meth)acrylic resin | Type | Synthesis Example 1 | Synthesis Example 1 | Synthesis Example 1 | Synthesis Example 1 | — | — | — | — |
| | Amount of mixing | 10 | 10 | 10 | 10 | — | — | — | — |
| Particle | Type | Spherical particle C | Spherical particle C | Spherical particle C | Spherical particle C | — | — | — | — |
| | Amount of mixing | 0.3 | 0.3 | 0.3 | 0.3 | — | — | — | — |
| Wet printing | | | | | | | | | |
| Offset resistance | Coated paper | | | ⊚ | | | | X | |
| | Matte paper | | | ⊚ | | | | X | |
| Time interval before printing on opposite face | 1 hour after | | | ○ | | | | X | |
| | 3 hours after | | | ○ | | | | X | |
| | 5 hour after | | | ○ | | | | Δ | |
| | 7 hours after | | | ○ | | | | ○ | |
| Time interval before cutting | 1 hour after | | | Δ | | | | X | |
| | 3 hours after | | | ○ | | | | Δ | |
| | 6 hours after | | | ○ | | | | ○ | |

TABLE 10-continued

| Ink composition | | Example 27 | Example 28 | Example 29 | Example 30 | Comparative Example 11 | Comparative Example 12 | Comparative Example 13 | Comparative Example 14 |
|---|---|---|---|---|---|---|---|---|---|
| Waterless printing | | | | | | | | | |
| Offset resistance | Coated paper | | | ⊚ | | | | | X |
| | Matte paper | | | ⊚ | | | | | X |
| Scumming resistance | Coated paper | | | ○ | | | | | X |

In Table 10, the values of the amount of mixing are given in "part(s) by weight".

As is clear from the results above, offset was found neither on the smooth fast-setting and slow-setting papers, nor on the matte papers with surface irregularity. In addition, owing to its fast drying property, the ink composition of this invention could largely shorten the time interval after printing on one face and before printing on the opposite face, leading to an improved productivity in printing.

INDUSTRIAL APPLICABILITY

The ink composition of this invention is not only greatly excellent in dryability as compared with the conventional product, but also enables production of printed matter unlikely to cause offset even if vertically stacked immediately after printing. The ink composition is particularly useful as an ink for sheetfed offset printing and overprint varnish.

With the ink composition of this invention, powder scattering during printing is no more necessary or may largely be reduced, unlike the conventional cases using oxidative polymerization drying oils based ink or OP varnish. In addition, the ink composition of this invention contributes to improve the productivity in printing, owing to its fast drying property. The ink composition of this invention does not need any new facility investment, since all of the conventional printing press and printing paper are employable.

The ink composition of this invention is suitably used as an offset printing ink responding to short delivery printing, and may be used in a variety of printing in the field of commercial business and publishing.

REFERENCE SIGNS LIST 1 petroleum solvent
2 printing paper
3 oxygen
4 colorant
5 binder resin
6 drying oil

We claim:

1. An ink composition comprising a (meth)acrylic resin and a drying oil,
   the (meth)acrylic resin:
      containing at least 40% by weight or more of a structural unit derived from (meth)acryl monomer having a straight-chain alkyl group having 4 or more carbon atoms, a branched alkyl group having 4 or more carbon atoms, or a cyclic alkyl group having 4 or more carbon atoms (1);
      having a glass transition temperature of 63° C. to 180° C. (2); and
      having a weight-average molecular weight of 1000 to 80,000 (3);

wherein the ink composition contains 1 to 10% by weight of the (meth)acrylic resin, 20 to 35% by weight of a binder resin, 10 to 40% by weight of the drying oil, 15 to 40% by weight of a solvent, 0.01 to 3% by weight of a dryer, and, 0.1 to 5% by weight of a wax.

2. The ink composition of claim 1, which contains the (meth)acrylic resin in a content of 2 to 6% by weight.

3. The ink composition of claim 1, which contains 2 to 6% by weight of the (meth)acrylic resin, 25 to 30% by weight of the binder resin, 15 to 35% by weight of the drying oil, 20 to 30% by weight of the solvent, 0.5 to 1.5% by weight of the dryer, and, 0.5 to 4% by weight of the wax.

4. An ink composition comprising a (meth)acrylic resin and a drying oil,
   the (meth)acrylic resin:
      containing at least 40% by weight or more of a structural unit derived from (meth)acryl monomer having a straight-chain alkyl group having 4 or more carbon atoms, a branched alkyl group having 4 or more carbon atoms, or a cyclic alkyl group having 4 or more carbon atoms (1);
      having a glass transition temperature of 63° C. to 180° C. (2); and
      having a weight-average molecular weight of 1000 to 80,000 (3), and
      the ink composition further containing a particle having an average size of 3.0 to 17.5 μm, and;
   relative to the ink composition, 0.01 to 1% by weight of a spherical particle having a particle size of 1.0 to 20.2 μm, and 0.1% by weight or less of a particle having a particle size exceeding 20.2 μm.

5. The ink composition of claim 1, further containing, relative to the ink composition, 0.01 to 1% by weight of a spherical particle having a particle size of 1.0 to 20.2 μm, and wherein the composition contains a particle having a particle size exceeding 20.2 μm in a content of 0.1% by weight or less.

6. The ink composition of claim 4, wherein the spherical particle is at least one species selected from an olefinic particle, a styrene-based particle, a phenolic particle, a silicone-based particle, a urethane-based particle and an acrylic particle.

7. The ink composition of claim 1, further containing 5 to 35% by weight of a colorant.

8. The ink composition of claim 1, which is adapted for offset printing.

9. The ink composition according to claim 1, which is adapted for oxidative polymerization based ink.

10. A printed matter obtained by using the ink composition described in claim 1.

11. A printing method comprising a step of printing using the ink composition described in claim 1.

12. The ink composition of claim 4, further containing 5 to 35% by weight of a colorant.

13. The ink composition of claim 5, wherein the spherical particle is at least one species selected from an olefinic particle, a styrene-based particle, a phenolic particle, a silicone-based particle, a urethane-based particle and an acrylic particle.

14. The ink composition of claim 5, further containing 5 to 35% by weight of a colorant.

* * * * *